(12) United States Patent
Mangeot et al.

(10) Patent No.: US 8,716,020 B2
(45) Date of Patent: *May 6, 2014

(54) REPROGRAMMATION OF EUKARYOTIC CELLS WITH ENGINEERED MICROVESICLES

(75) Inventors: Philippe Mangeot, Lyon Cedex (FR); Vincent Lotteau, Lyon Cedex (FR); Marc Peschanski, Evry Cedex (FR); Mathilde Girard, Evry Cedex (FR)

(73) Assignee: INSERM (Institut National de la Sante et de la Recherche Medicale), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/505,934

(22) PCT Filed: Nov. 10, 2010

(86) PCT No.: PCT/EP2010/067225
§ 371 (c)(1),
(2), (4) Date: Oct. 22, 2012

(87) PCT Pub. No.: WO2011/058064
PCT Pub. Date: May 19, 2011

(65) Prior Publication Data
US 2013/0034900 A1 Feb. 7, 2013

(30) Foreign Application Priority Data
Nov. 13, 2009 (EP) .................................... 09306092

(51) Int. Cl.
*C12N 5/07* (2010.01)
*C12N 5/073* (2010.01)

(52) U.S. Cl.
USPC ........................................ 435/377; 435/325

(58) Field of Classification Search
USPC ................................. 435/377, 325
See application file for complete search history.

(56) References Cited

FOREIGN PATENT DOCUMENTS

WO 2006/059141 6/2006
WO 2009/032194 3/2009

OTHER PUBLICATIONS

Abe Akihiro et al., "Enhanced gene transfer with fusogenic liposomes containing vesicular stomatitis virus G glycoprotein," J. Virol., 72(7):6159-6163 (1998) XP002614185.
Clarke et al., "A safer stem cell: inducing pluripotency," Nat. Med., 15(9):1001-1002 (2009) XP002614186.
International Search Report and Written Opinion in PCT/EP2010/067225, dated Jan. 20, 2011.
Kaji et al., "Virus-free induction of pluripotency and subsequent excision of reprogramming factors," Nature, 458 (7239):771-775 (2009).
Kim Dohoon et al., "Generation of human induced pluripotent stem cells by direct delivery of reprogramming proteins," Cell Stem Cell, 4(6):472-476 (2009) XP002564507.
Lyssiotis et al., "Reprogramming of murine fibroblasts to induced pluripotent stem cells with chemical complementation of Klf4," Proc. Natl. Acad. Sci. USA, 106(22):8912-8917 (2009).
Park In-Hyun et al., "Reprogramming of human somatic cells to pluripotency with defined factors," Nature, 451 (7175):141-147 (2007) XP002475655.
Ratajczak et al., "Embryonic stem cell-derived microvesicles reprogram hematopoietic progenitors: evidence for horizontal transfer of mRNA and protein delivery," Leukemia, 20(5):847-856 (2006) XP002456317.
Rolletschek et al., "Induced human pluripotent stem cells: promises and open questions," Biol. Chem., 390(9):845-849 (2009) XP002614187.
Takahashi Kazutoshi et al., "Induction of pluripotent stem cells from adult human fibroblasts by defined factors," Cell, 131(5):861-872 (2007) XP002478584.
Temchura et al., "Enhancement of immunostimulatory properties of exosomal vaccines by incorporation of fusion-competent G protein of vesicular stomatitis virus," Vaccine, 26(29-30):3662-3672 (2003) XP022735985.
Yuan et al., "Transfer of MicroRNAs by Embryonic Stem Cell Microvesicles," PLOS One, 4(3):E4722-1 (2009) XP002562228.
Zhou et al., "Generation of induced pluripotent stem cells using recombinant proteins," Cell Stem Cell, 4(5):381-384 (2009).

*Primary Examiner* — Marcia S Noble
(74) *Attorney, Agent, or Firm* — McAndrews, Held & Malloy Ltd.

(57) ABSTRACT

The present invention relates to a non-genetic, detergent-free, bacteria-free method for reprogramming a eukaryotic cell, in particular for obtaining induced pluripotent stem cells (iPS), by using engineered microvesicles carrying at least one reprogramming transcription factor, wherein said engineered microvesicles are virus-free.

7 Claims, 16 Drawing Sheets

Figure 1

A

B

A

B

C

D

US 8,716,020 B2

REPROGRAMMATION OF EUKARYOTIC CELLS WITH ENGINEERED MICROVESICLES

Figure 2:
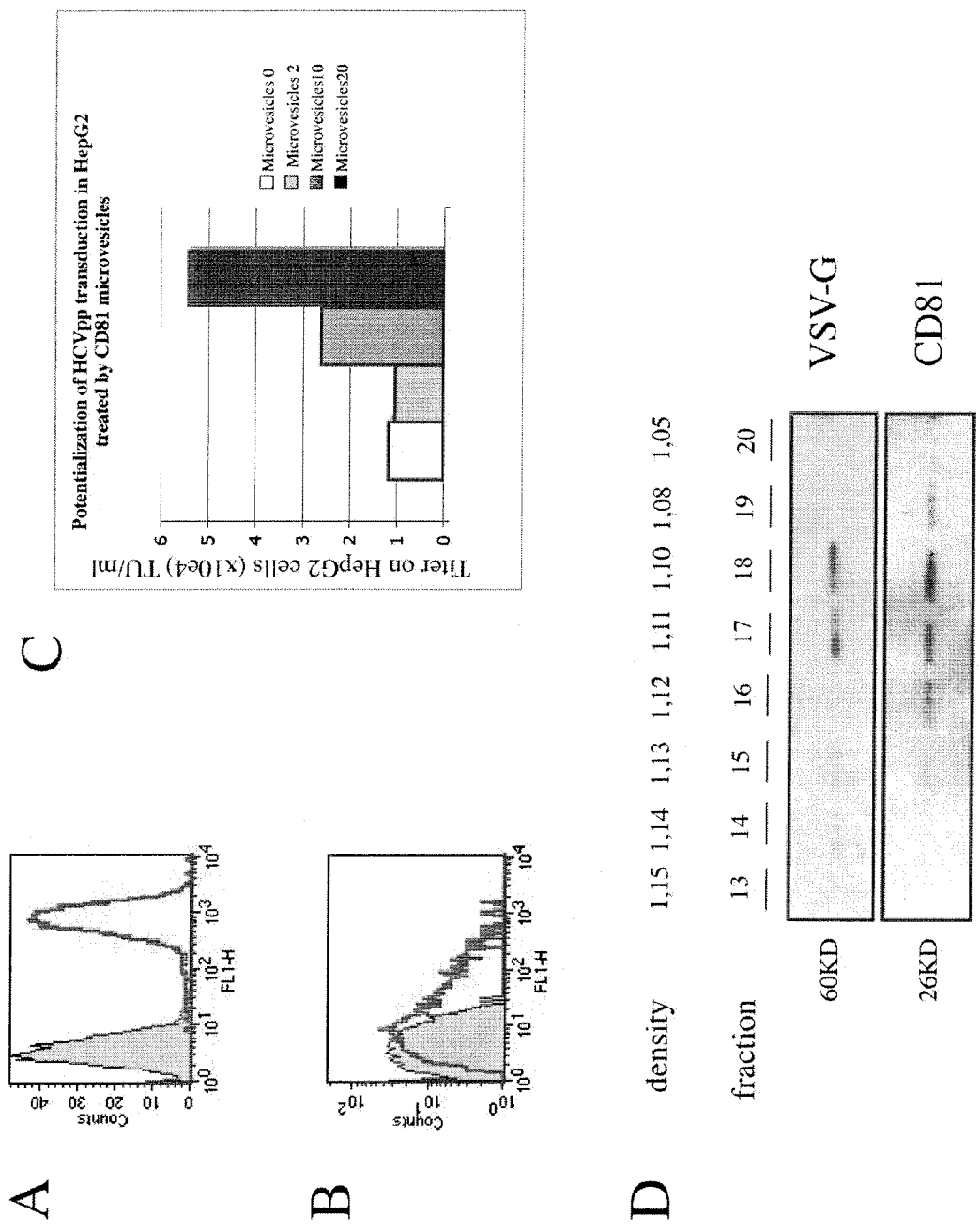

The present application is filed pursuant to 35 U.S.C. 371 as a U.S. National Phase application of International Patent Application No. PCT/EP2010/067225, which was filed Nov. 10, 2010, claiming the benefit of priority to European Patent Application No. 09306092.9, which was filed on Nov. 13, 2009. The entire text of the aforementioned applications is incorporated herein by reference in its entirety.

FIELD OF THE INVENTION

The present invention relates to a method for reprogramming a eukaryotic cell, in particular for obtaining induced pluripotent stem cells (iPS cells).

BACKGROUND OF THE INVENTION

Mammalian cells are a widely used in vitro model in diagnostic and medical applications. For example, mammalian cells may be used for screening drugs, studying molecular pathways, or for the production of therapeutics drugs. Mammalian cells can also be used for cell therapy.

Mammalian stem cells are primal cells found in all mammalian organisms that retain the ability to renew themselves through mitotic cell division and can differentiate into a diverse range of specialized cell types. Embryonic stem cells (ES cells) are cultures of cells derived from the epiblast tissue of the inner cell mass of a blastocyst.

Due to their two fundamental attributes of unlimited expansion and pluripotency, stem cells, and in particular human embryonic stem (hES) cells have gained considerable interest for use in cell replacement therapy as well as in drug discovery.

However, the use of embryos for obtaining of ES cells is controversial and raises ethical issues. Alternative sources of pluripotent cells have therefore been investigated.

Induced pluripotent stem cells (iPS cells) are a type of pluripotent stem cells artificially derived from a non-pluripotent, typically an adult somatic cell, by inducing a "forced" expression of certain genes.

iPS cells were first produced in 2006 from mouse cells (Takahashi et al Cell 2006 126:663-76) and in 2007 from human cells (Takahashi et al. Cell 2007 131-861-72, Yu et al. Science 2007 318:1917). These authors demonstrated that it was possible to de-differentiate somatic cells by introducing reprogramming transcription factors into said somatic cells using a viral expression system.

However, the use of viral transduction poses several problems that hinder the development of such methods for use in therapy. Indeed, there exists a risk of genomic alteration of the target cell, and of oncogene expression.

Other authors have suggested the use of non-integrating episomal vectors for producing virus-free iPS cells (Yu et al. Science 2009, vol 324, p 797-801). However, the reprogramming efficiency remains low. Further, karyotype anomalies in one of the resulting iPS clones were later observed by these authors.

Recently, Zhou et al. have reported a non-genetic method for obtaining iPS cells (Zhou et al. Cell Stem Cell 2009, vol 4, p 381-384). These authors used poly-arginine recombinant proteins in order to introduce reprogramming factors into a target cell. However, this method is time-consuming and poorly amenable to large scale production, since each recombinant protein must be expressed and purified before introduction into the target cell.

Thus, there is still a need in the art for a fast, safe and efficient method for reprogramming a target cell, for example for obtaining induced pluripotent stem cells.

SUMMARY OF THE INVENTION

The present invention relates to a eukaryotic cell overexpressing a viral membrane fusion protein and reprogramming transcription factor.

The present invention also relates to a microvesicle secreted by a eukaryotic cell according to the invention, wherein said microvesicle comprises said viral membrane fusion protein and said reprogramming transcription factor.

The invention also relates to a method for obtaining an induced pluripotent stem cell comprising the steps of:
  delivering an EcoR ecotropic viral receptor to a target cell by a microvesicle comprising a viral membrane fusion protein and said EcoR ecotropic viral receptor;
  delivering at least one reprogramming factor to said target cell by an ecotropic virus comprising at least one gene encoding a reprogramming factor.

The present invention also relates to an in vitro method for delivering a reprogramming transcription factor into a target cell by contacting said target cell with a microvesicle of the invention comprising said reprogramming transcription factor.

The invention also relates to a method for obtaining an induced pluripotent stem cell comprising the step of delivering at least one reprogramming factor to a target cell by a microvesicle as described above.

The invention also relates to an induced pluripotent stem cell obtainable by the methods described above.

DETAILED DESCRIPTION OF THE INVENTION

The inventors have discovered that the overexpression of a viral membrane fusion protein in a eukaryotic cell expressing a protein of interest can lead to the secretion of microvesicles comprising said membrane fusion protein and said protein of interest. Further, the inventors have demonstrated that said microvesicles can be used to efficiently deliver said protein of interest to a target cell.

In particular, they have demonstrated that microvesicles can be used to deliver an ecotropic receptor to a target cell, thereby rendering said target cell permissive to an ecotropic virus containing a reprogramming transcription factor.

They have also demonstrated that microvesicles can be used to deliver directly a reprogramming transcription factor to a target cell, without altering the function of said reprogramming transcription factor, and thereby to reprogram said target cell, for example to obtain induced pluripotent stem cells.

Thus, the present invention relates to a eukaryotic cell overexpressing a viral membrane fusion protein and an ecotropic receptor or a reprogramming transcription factor. Said eukaryotic cell is capable of secreting microvesicles comprising said viral membrane fusion and ecotropic receptor or said reprogramming transcription factor.

In one embodiment, the eukaryotic cell according to the invention does not express any viral structural protein and the microvesicles secreted by such eukaryotic cells do not comprise any viral structural protein. Accordingly, the microvesicles according to the invention differ in that aspect from the virus-like particles (VLPs) described in the art, for example, in WO2006/059141, said VLPs comprising viral structural proteins, such as HIV1 Gag.

As used herein, the term "viral structural protein" refers to viral proteins that contribute to the overall structure of the capsid protein or of the protein core of a virus. The term "viral structural protein" further includes functional fragments or derivatives of such viral protein contributing to the structure of a capsid protein or of protein core of a virus. An example of viral structural protein is HIV1 Gag. The viral membrane fusion proteins are not considered as viral structural proteins. Typically, said viral structural proteins are localized inside the microvesicles.

The inventors have indeed shown that microvesicles comprising a protein of interest can be produced in eukaryotic cells that do not express any viral structural protein but overexpress a membrane fusion protein, such as VSV-G or other fusogenic proteins, and said reprogramming transcription factor.

Moreover, the microvesicles according to the invention may not contain any nucleic acid encoding for the reprogramming transcription factor. Of course, one can not exclude that traces of nucleic acid are contained in said microvesicles, in particular traces of mRNA from producer cells or even DNA resulting from previous transfection. However, the inventors have demonstrated that such traces of nucleic acids (if exits) cannot be responsible for at least 90% of the protein function transfer by microvesicles.

Typically the eukaryotic cell is a mammalian cell, such as a human cell, or an insect cell.

Examples of suitable mammalian cells are, but are not limited to HEK-293T cells, COS7 cells, Hela cells and HEK-293 cells.

By "overexpressing", it is meant any means known in the art to enhance the amount of protein expressed by a given cell. Practically, the viral membrane fusion protein and the reprogramming transcription factor are expressed to a level so that said eukaryotic cells are capable of secreting microvesicles comprising said viral membrane fusion protein and said reprogramming transcription factor without the need of expressing any viral structural protein.

Typically, the overexpression of the viral membrane fusion protein and of the reprogramming transcription factor may be achieved by transfecting the eukaryotic cell with an expression vector encoding the viral membrane fusion protein and an expression vector encoding the reprogramming transcription factor.

In another embodiment, said eukaryotic cell according to the invention is overexpressing VSV-G as a viral membrane fusion protein and the reprogramming transcription factor but does not overexpress any other viral proteins, in particular any viral structural protein. The microvesicles secreted according to said embodiment comprise VSV-G and said reprogramming transcription factor but do not comprise any viral structural protein.

In another specific embodiment, the eukaryotic cells overexpress only the viral membrane fusion protein and said reprogramming transcription factor. In this embodiment, expression of the viral membrane fusion protein, for example VSV-G, may represent at least 30%, for example at least 50%, of the overexpressed proteins in the cells.

In one embodiment, said viral membrane fusion protein and said reprogramming transcription factor can be encoded by two different vectors.

In one embodiment, said viral membrane fusion protein and said protein of interest can be carried by a single vector containing a bicistronic expression cassette. In a related embodiment; said viral membrane fusion protein and said reprogramming transcription factor are not covalently bonded together.

In one embodiment, expression vectors may include episomal replicating plasmids and, for example, plasmids comprising origin sequence of viral nature such as SV40 ORI or EBV ORI sequences.

Overexpression via expression vectors can comprise any gene transfer method known in the art of molecular biology.

In a preferred embodiment, overexpression is obtained by transfection of an exogenous DNA. Suitable transfection methods are classical methods known to the skilled person, such as calcium phosphate transfection, transfection using liposomes (also known as lipofection) or electroporation. It falls within the ability of the skilled person to select the appropriate transfection method for a given cell.

In a preferred embodiment, overexpression is not obtained by viral transduction.

Overexpression can be transient overexpression or stable overexpression.

When transient overexpression is used, cells typically overexpress optimum amounts of the viral membrane fusion protein and/or the reprogramming transcription factor between 48 and 72 hours post-transfection.

The term "overexpression" also covers the overexpression of an endogenous protein, i.e. a protein which is naturally expressed by the eukaryotic cell. The overexpression can consist either in the introduction of additional copies of the gene encoding said protein or in the stimulation of the expression of the endogenous protein. By way of example, the eukaryotic cell can be placed under culture conditions known to enhance the expression of said endogenous protein.

Typically, said viral membrane fusion protein is a class I viral membrane fusion protein such as the influenza-virus hemagglutinin, a class II viral membrane fusion protein or a class III viral membrane fusion protein (see for review on class III viral membrane fusion protein Backovic et al, Curr Opin Struct Biol 2009, 19(2):189-96 or Courtney et al, Virology Journal 2008, 5:28).

In a preferred embodiment, said viral membrane fusion protein is a class I viral membrane fusion protein.

Examples of class I viral membrane fusion proteins are Baculovirus F proteins, in particular F proteins of the nucleopolyhedrovirus (NPV) genera, such as *Spodoptera exigua* MNPV (SeMNPV) F protein and *Lymantria dispar* MNPV (LdMNPV) F protein.

In a preferred embodiment said viral membrane fusion protein is a class III viral membrane fusion protein.

Examples of class III viral membrane fusion proteins are rhabdovirus G (such as the fusogenic protein G of the Vesicular Stomatatis Virus (VSV-G)), herpesvirus gB (such as the glycoprotein B of Herpes Simplex virus 1 (HSV-1 gB)), EBV gB, thogotovirus G, baculovirus gp64 (such as *Autographa California* multiple NPV (AcMNPV) gp64), and the Borna disease virus (BDV) glycoprotein (BDV G).

In a more preferred embodiment said viral membrane fusion protein is VSV-G or baculovirus gp64. In one embodiment, said viral membrane fusion protein is VSV-G polypeptide as defined in GenBank AN: M35219.1 or any functional fragments or their functional derivatives retaining fusogenic properties.

As used herein, the term "fusogenic" refers to the capacity of a protein to induce the fusion of the plasma membrane of the microvesicles to the membrane of the target cell.

In an embodiment of the invention, the eukaryotic cell according to the invention further overexpresses a protein which induces membrane budding. In this embodiment, the production of microvesicles is enhanced.

As used herein, the expression "protein which induces membrane budding" refers to any protein which can promote the deformation of lipid bilayers and mediate the formation of vesicles.

The ability of a given test protein to induce membrane budding can be evaluated according to the following in vitro test "A":

HEK293T cells are transfected with the test protein or mock-transfected with an empty vector. 20 hours post-transfection the cell media are replaced with R18-containing medium (20 μg/ml). R18, or octadecyl rhodamine B chloride, is a lipophilic compound that binds membranes and emits fluorescence at 590 nm upon excitation at 560 nm. After 6 hours of incubation, to allow R18 incorporation into cell membranes, media are changed from fresh medium without R18. 72 hours post-transfection, media from the transfected cells and from the mock-transfected cells are collected, clarified and analyzed by a fluorometer. The amount of R18-associated fluorescence, normalized to the number of living cells counted by a rezazurin-based assay, reflects the amount of membrane released by the cells in each condition.

A test protein is deemed to induce membrane budding if it increases the amount of R18-associated fluorescence per cell, as measured by the above test "A".

Various cellular and viral proteins are known to induce membrane budding.

Examples of cellular proteins inducing membrane budding are the proteolipid protein PLP1 (Trajkovic et al. 2008 Science, vol 319, p 1244-1247), the clathrin adaptor complex AP1 (Camus et al., 2007. Mol Biol Cell vol 18, p 3193-3203), proteins modifying lipid properties such as floppase, scramblase, proteins which facilitate the secretion via a non-classical pathway such as TSAP6 (Yu et al. 2006 Cancer Res vol 66, p 4795-4801) and CHMP4C (Yu et al. 2009, FEBS J. vol 276, p 2201-2212).

Examples of viral proteins inducing membrane budding are tetherin/CD317 antagonists such as the Vpu protein of HIV (Neil et al. 2008. Nature vol 451, p 425-4431) and various viral structural proteins such as retroviral GAG (Camus et al., 2007. Mol Biol Cell vol 18, p 3193-3203) and Ebola VP40 (Timmins et al., Virology 2001).

Membrane budding may also be induced by modifying the cell culture conditions of the eukaryotic cell overexpressing a viral membrane fusion protein and a reprogramming factor, such as temperature, $Ca^{2+}$ concentration, etc.

In an embodiment of the invention, the eukaryotic cell overexpresses 2 to 5 different reprogramming factors.

As used herein, the expressions "reprogramming factors", "reprogramming nuclear factor" and "reprogramming transcription factor" are used interchangeably. They refer to nuclear proteins that, when expressed in a given target cell, independently or in combination, can be used to change the cell's fate, i.e. to re-program the cell.

Reprogramming factors for obtaining induced pluripotent stem cells (iPS) have been described in the prior art.

For example, reprogramming factors have been identified in document WO2007/069666. Reprogramming factors are described in Takahashi et al Cell 2006 126: 663-76; Takahashi et al. Cell 2007 131-861-72 and Yu et al. Science 2007 318: 1917.

Reprogramming transcription factors can be of any mammalian origin. Typically, they can be of murine origin or of human origin. Preferably, the reprogramming transcription factors belong to the same species as the target cell which is to be reprogrammed Examples of reprogramming factors include, but are not limited to:

Oct-3/4 (Pou5f1): Oct-3/4 is one of the family of octamer ("Oct") transcription factors, and plays a crucial role in maintaining pluripotency. The absence of Oct-3/4 in Oct-3/4+ cells, such as blastomeres and embryonic stem cells, leads to spontaneous trophoblast differentiation, and presence of Oct-3/4 thus gives rise to the pluripotency and differentiation potential of embryonic stem cells. Exemplary Oct3/4 proteins are the proteins encoded by the murine Oct3/4 gene (Genbank accession number NM 013633) and the human Oct3/4 gene (Genbank accession number NM 002701).

Factors of the Sox family: The Sox family of genes is associated with maintaining pluripotency similar to Oct-3/4, although it is associated with multipotent and unipotent stem cells in contrast with Oct-3/4, which is exclusively expressed in pluripotent stem cells. While Sox2 was the initial gene used for induction (Takahashi et al Cell 2006 126: 663-76; Takahashi et al. Cell 2007 131-861-72; Yu et al. Science 2007 318:1917), other genes in the Sox family have been found to work as well in the induction process. Sox1 yields iPS cells with a similar efficiency as Sox2, and genes Sox3, Sox15, and Sox18 also generate iPS cells.

Exemplary sox-2 proteins are the proteins encoded by the murine Sox2 gene (Genbank accession number NM_011443) and the human Sox2 gene (Genbank accession number NM_003106).

Factors of the Klf family: Klf4 of the Klf family of genes was initially identified as a factor for the generation of mouse iPS cells and was also demonstrated to be a factor for generation of human iPS cells.

Exemplary Klf4 proteins are the proteins encoded by the murine klf4 gene (Genbank accession number NM_010637) and the human klf4 gene (Genbank accession number NM_004235).

Factors of the Myc family: The Myc family of genes contains proto-oncogenes implicated in cancer. c-myc was shown to be a factor implicated in the generation of mouse iPS cells and of human iPS cells.

Exemplary c-myc proteins are the proteins encoded by the murine c-myc gene (Genbank accession number NM_010849) and the human c-myc gene (Genbank accession number NM_002467).

The Nanog family: In embryonic stem cells, Nanog, along with Oct-3/4 and Sox2, is necessary in promoting pluripotency.

LIN28: LIN28 is an mRNA binding protein expressed in embryonic stem cells and embryonic carcinoma cells associated with differentiation and proliferation. Yu et al. demonstrated it is a factor in iPS generation, although it is not mandatory (Yu et al. Science 2007, vol 318: 1917-20).

Advantageously, the inventors have shown that the reprogramming transcription factor retains its functionality once it has been transferred into the target cell.

In one embodiment, the viral membrane fusion protein can contain a tag which enables the purification of the microvesicles released from the eukaryotic cell. Said tag can be located for example in the ectodomain of the viral membrane fusion protein.

Suitable tags include, but are not limited to: Flag tag, HA tag, GST tag, His6 tag. It falls within the ability of the skilled person in the art to select the appropriate tag and the appropriate purification method of said tag.

Suitable purification methods include, but are not limited to immunoprecipitation, affinity chromatography, and magnetic beads coated with anti-tag specific antibody.

In a preferred embodiment, the eukaryotic cell according to the invention is virus-free.

The present invention also relates to a microvesicle secreted by a eukaryotic cell according to the invention, wherein said microvesicle comprises said viral membrane fusion protein and said reprogramming transcription factor.

Without wishing to be bound by theory, said microvesicles are considered to be exosome-like and to have a size between 40 and 150 nm, for example between 40 and 100 nm, for example an average size of about 100 nm. Typically a microvesicle according to the invention has a density between 1.08 g/ml and 1.12 g/ml.

Preferably a microvesicle according to the invention has a density between 1.09 g/ml and 1.11 g/ml. Typically, said density can be measured by sedimentation on a continuous iodixanol gradient as defined in Example 1.

When transient overexpression of the viral membrane fusion protein and/or of the reprogramming transcription factor is used, microvesicles are typically harvested from the cell supernatant 48-72 hours post-transfection.

Typically the microvesicles according to the invention may be isolated by filtration (for example on 0.45 µm pore filters) of the cell supernatant of eukaryotic cells according to the invention and ultracentrifugation for example, by ultracentrifugation at 110,000 g for 1.5 hours.

Advantageously, the microvesicles according to the invention may be frozen and stored at −80° C. without losing their ability to transfer material to the target cell.

In another embodiment, said microvesicles according to the invention do not comprise any nucleic acid coding for said reprogramming transcription factor.

In a preferred embodiment, a microvesicle according to the invention is virus free.

Firstly described for immune system cells, microvesicles released from cells are found in vivo in many body fluids (Simpson et al. *Proteomics* 8, 4083-4099 (2008)). Many studies have highlighted the role of these microvesicles in the modulation of the immune response and intercellular communication.

Without wishing to be bound by theory, it is believed that the microvesicles of the invention are exosome-like vesicles, and the presence of the viral membrane fusion protein enables said microvesicles to efficiently deliver the material contained in said microvesicles to the target cell.

The present invention also relates to a method for obtaining an induced pluripotent stem cell comprising the steps of:
  delivering an EcoR ecotropic viral receptor to a target cell by a microvesicle comprising a viral membrane fusion protein and said EcoR ecotropic viral receptor;
  delivering at least one reprogramming factor to said target cell by an ecotropic virus comprising at least one gene encoding a reprogramming factor.

As used herein, the term "ecotropic" has its general meaning in the art. An ecotropic virus is a retrovirus which can replicate only in the host of the species in which it originated. More specifically, the term "ecotropic virus" as used herein refers to a rodent virus that can only replicate in a cell expressing its cognate receptor, the ecotropic receptor EcoR.

Advantageously, said ecotropic virus is safe for the manipulator and for the environment since it cannot infect human cells other than those which have been targeted by a microvesicle expressing the ecotropic viral receptor. This increased biosafety means that it can manipulated without any risk of contamination.

Typically, said ecotropic virus is a Moloney-based retrovirus and said ecotropic receptor is m-CAT1. An example of a gene coding for m-CAT1 is shown in Genbank accession number NCBI Reference sequence NM_007513.3.

The present invention also relates to an in vitro method for delivering a reprogramming transcription factor into a target cell by contacting said target cell with a microvesicle of the invention comprising said reprogramming transcription factor.

The invention therefore relates to a method for obtaining an induced pluripotent stem cell comprising the step of delivering at least one reprogramming factor to a target cell by a microvesicle as described above.

Examples of target cells are somatic cells obtained from primary cultures. Typically, said target cell is a fibroblast of any origin in the body or any other cell capable of proliferation after plating in vitro in culture conditions.

The tropism of the microvesicles of the invention will depend on the tropism of the viral membrane fusion protein used.

For example, VSV-G being a pantropic, microvesicles according to the invention comprising VSV-G will target almost any cells. Microvesicles comprising a viral membrane fusion protein with a tropism for respiratory tract cells will preferably be used to target respiratory tract cells.

In one embodiment, the target cell is patient-specific.

In this embodiment, the method of the invention can be used to generate patient-specific iPS cells.

For instance, iPS cells can be obtained from patients affected with Fanconi anemia (Raya et al. Nature 2009, 460: 53-59); adenosine desaminase immune deficit (ADA-SCID), Gaucher's disease, muscular dystrophy, Parkinson's disease, Huntington's disease etc. Patient-specific iPS cells represent a valuable model to study diseases.

Moreover they are of great interest in regenerative therapy, since they represent a potentially unlimited source of autogenic cells that can be expanded and further re-differentiated into any given tissue.

In a preferred embodiment the microvesicles according to the invention are produced in situ, by co-culture of the target cells with the microvesicles producing cells. In one specific embodiment, the target cells and the microvesicles producing cells are physically located in two different compartments separated by porous wall, wherein said porous wall has pores with a diameter smaller than the diameter of eukaryotic cells but bigger than the diameter of microvesicles of interest. Advantageously, the microvesicles as produced by the eukaryotic cells according to the invention can diffuse from one compartment to the other to reach the target cells where they can deliver the reprogramming factors but the microvesicles producing cells remains separated from the target cells.

This technique enables the delivery of protein into target cells, without the need of an isolating step.

Typically several (e.g., 2, 3, 4, 5, 6 . . . ) different reprogramming transcription factor may be delivered into a target cell by contacting said target cell with several different microvesicles of the invention comprising said several different reprogramming transcription factor such as, but not limited to Oct-4, KLF4, sox2, Lin28 and c-myc.

In one embodiment, the invention relates to a method for obtaining an iPS from a target cell comprising the step(s) of contacting said target cell with microvesicles comprising at least one reprogramming transcription factor selected from the group consisting of Oct-4, KLF4, sox2, Lin28 and c-myc.

Advantageously, each microvesicle comprises no more than two types of reprogramming transcription factors, for example only one type of reprogramming transcription factor.

In a preferred embodiment, the invention relates to a method for obtaining an iPS from a target cell comprising the step(s) of contacting said target cell with microvesicles comprising Oct-4, microvesicles comprising KLF4, microvesicles comprising sox2, microvesicles comprising Lin28 and/or microvesicles comprising c-myc.

Typically, the contacting of said several different microvesicles may be simultaneous or sequential.

Due to the low amounts of material delivered by the microvesicles according to the invention and to their non-genetic nature, the microvesicles are useful for applications where low and transient presence of proteins may lead to striking biological effects, as is the case of reprogramming transcription factors.

Advantageously, the method for obtaining iPS cells according to the invention is safe, since it does not require the use of viral vectors. Moreover, due to the non-genetic nature of the microvesicles of the invention, there is no risk of genome modification. Compared to methods using recombinant proteins, there is no risk linked to the expression system (often bacterial expression systems), or to the purification of said recombinant protein (loss of function of the reprogramming factor, use of detergents etc.).

Advantageously, the IPS cells obtainable by the method of the invention are virus-free, bacteria-free and detergent-free.

Thus, the invention relates to induced pluripotent stem (iPS) cells obtainable by the method described above.

The invention also relates to the use of iPS cells as described above for testing drugs for toxic effects or for any high/medium/low throughput/content screening in the drug discovery process for the pharmaceutical and cosmetic industry. The invention also relates to iPS cells as described above for use in therapy for allografting in any form of regenerative medicine.

In the following, the invention will be illustrated by means of the following examples and figures.

FIGURES LEGENDS

Figure 1:
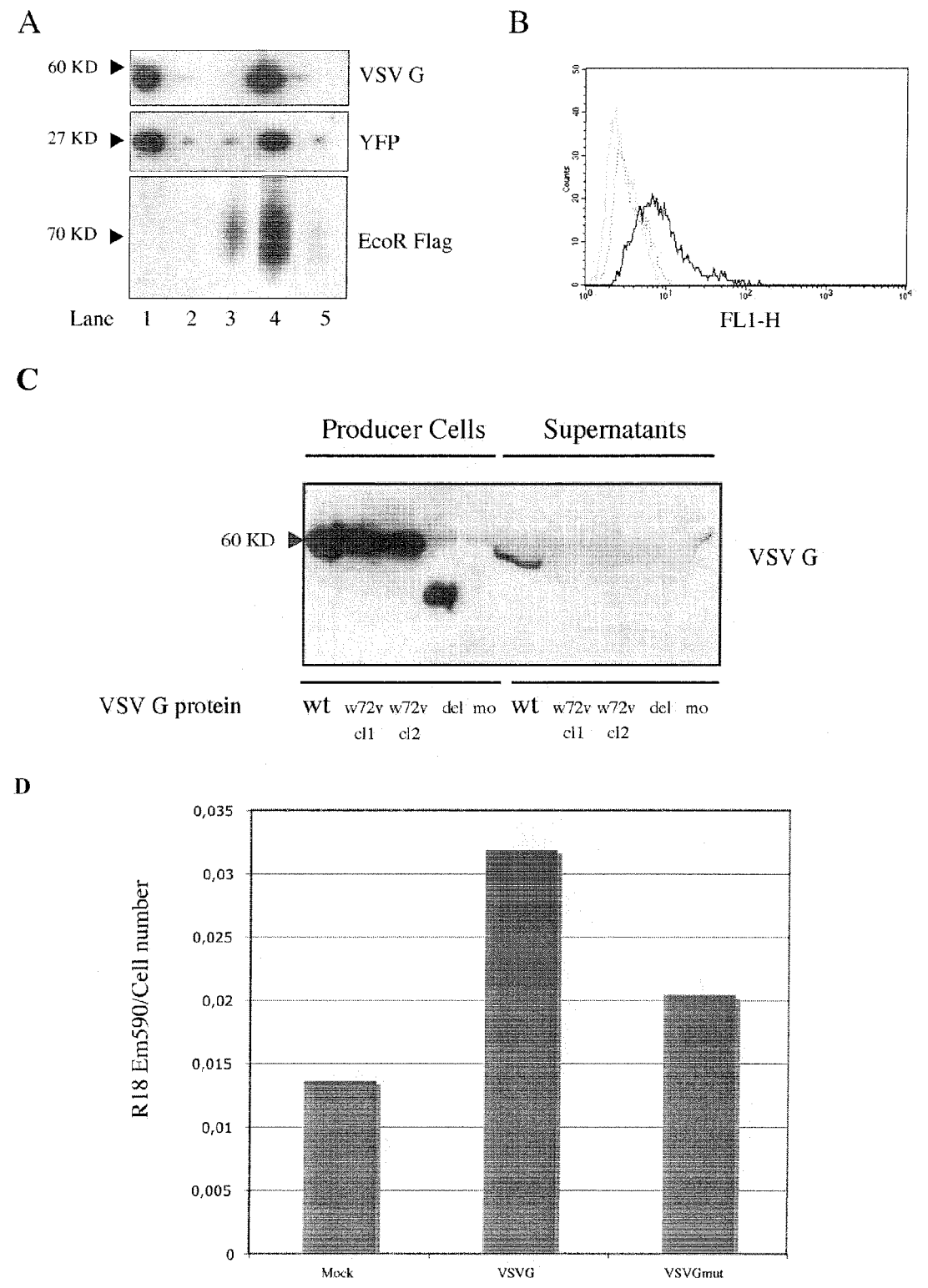

FIG. 1: Incorporation of YFP in VSV-G Carrying Microvesicles
(A) Western blot analysis of concentrated microvesicles produced by 293T-YFP transfected by pVSV-G (lane 1), pVSV-G V72 (lane 2), SwFlagEcoR (lane 3), SwFlagEcoR and pVSV-G (lane 4) and mock transfected (lane 5) Immunostainings were performed with Mabs directed against VSV-G (P5D4), the Sigma flag (M2) revealing the tagged version of EcoR and YFP (GSN24).
(B) FACS analysis of cells exposed to the microvesicles from the VSV-G and YFP expressing cells, compared to cells exposed to microvesicles from cells expressing YFP alone.
(C) HEK cells were transfected either by a plasmid encoding the wild-type VSV-G protein (wt) or a fusion-defective mutant W72V (2 DNA clones were tested). A truncated form of VSV-G deleted for its ectodomain was also included in the experiment. 48 h after transfection, supernatants were harvested and cells lysed for a Western blot analysis. All proteins were highly expressed in the producer cells. However, only the wt VSV-G was detected in the supernatant and not the fusion defective mutant.
(D) HEK cells were transfected as above and incubated, 20 hours post-transfection, in a medium containing 0.2 µg/ml of R18, a fluorescent lipophilic compound which binds to membranes, for 6 hours. 72 hours post-transfection, media from the different cell types were collected, clarified and the analyzed by a fluorometer to quantify the amount of R18-associated fluorescence, reflecting the amount of membranes released into the supernatant. Results are given as the R18 value, normalized by the number of living cells.

FIG. 2: Biochemical and Functional Analysis of CD81NSV-G Coated Microvesicles
(A) CD81 expression on 293T producer cells. A mouse IgG isotypic control was used (shaded area).
(B) CD81 expression on HepG2 cells exposed to concentrated microvesicles, one hour after treatment. Non-treated HepG2 were labelled as well (grey shaded control).
(C) Potentiation of HCVpp transduction in HepG2 cells treated with various doses of microvesicles. YFO encoding HCVpp were produced in 293 cells and pre-titrated on HUH 7.2 cells at 8×10e4 transduction units (TU) per ml. The figure gives the titers in HepG2 which increases with the amount of microvesicles they have been exposed to.
(D) Density analysis of CD81-bearing microvesicles. Microvesicles were produced in 293T cells cultured with octadecylrhodamine B chloride (R18), a fluorophore labelling membrane lipids. Concentrated microvesicles were laid on a continuous iodixanol gradient and centrifuged 12 hours at 41000 rpm in a SW41 rotor. 20 fractions of 0.5 ml were then collected and 1/20 of each fraction was analyzed by Western blot under semi-native conditions. VSV-G and CD81 immunolabellings are shown for fractions 13 to 20 and were absent from other fractions (not shown).

Figure 3:
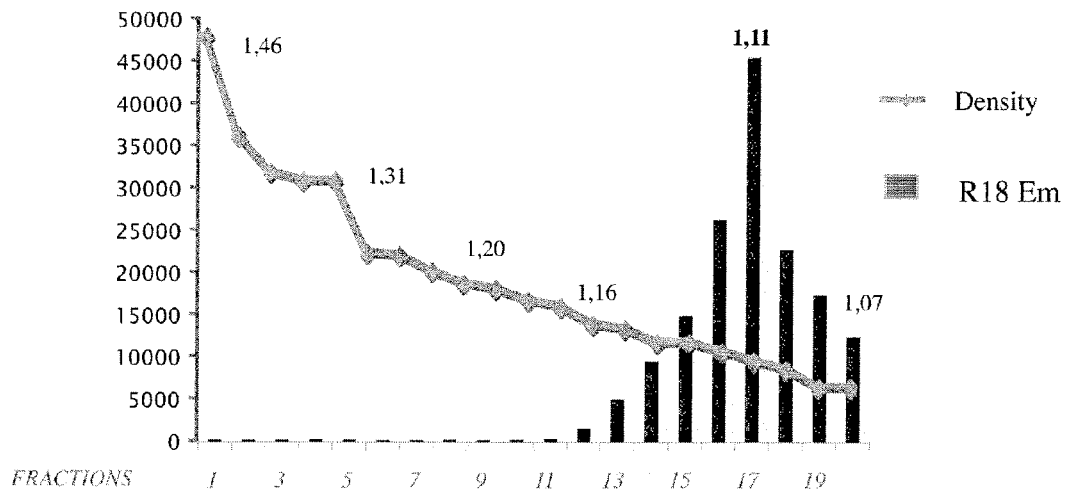
Figure 3:
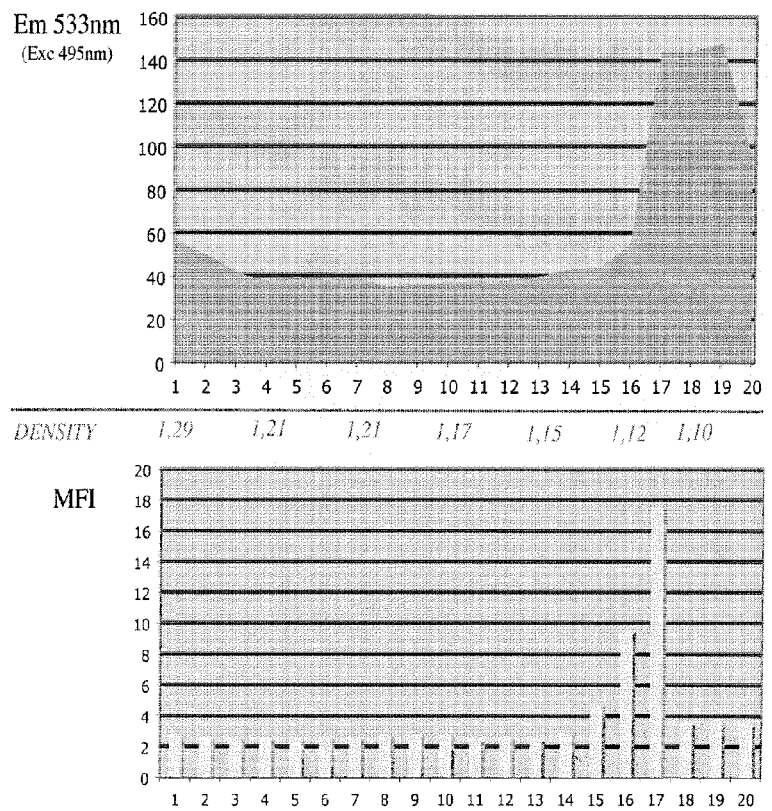

FIG. 3: Characterization of Gesicles
(A) Membrane-associated fluorescence in collected fractions upon density iodixanol gradient. Concentrated VSV-G Gesicles were laid on a continuous iodixanol gradient and centrifuged 3 hours. 20 fractions of 500 µl were collected from the bottom of the tube, fraction 1 corresponding to a density of 1.46 and fraction 20 to a density of 1.07 as indicated. 1/5 of each fraction (100 µl) were weighed and transferred to a 96 well plate prior to analysis in a fluorimeter. The figure gives the emission values at 590 nm upon R18 excitation at 560 nm.
(B) Characterization of YFP and CD81 bearing Gesicles
Top panel: analysis of YFP-associated fluorescence in collected fractions upon density gradient. Concentrated VSV-G Gesicles produced in YFP-positive cells were laid on a continuous iodixanol gradient and centrifuged 3 hours. 20 fractions of 500 µl were collected from the bottom of the tube, fraction 1 corresponding to a density of 1.3 and fraction 20 to a density of 1.09 as indicated. 1/5 of each fraction (100 µl) were weighed and transferred to a 96 well plate prior to analysis in a fluorimeter. The figure gives the emission values at 533 nm upon YFP excitation at 495 nm.
Lower panel: Analysis of YFP pseudotransduction in human cells. 1/10 of each fraction was laid on 1×10e5 HEK cells cultivated in a 12-well plate. 24 hours later, cells were analyzed by FACS. The figure indicates the mean fluorescence intensity (MFI) of each cell population exposed to the different fractions.

Figure 4:
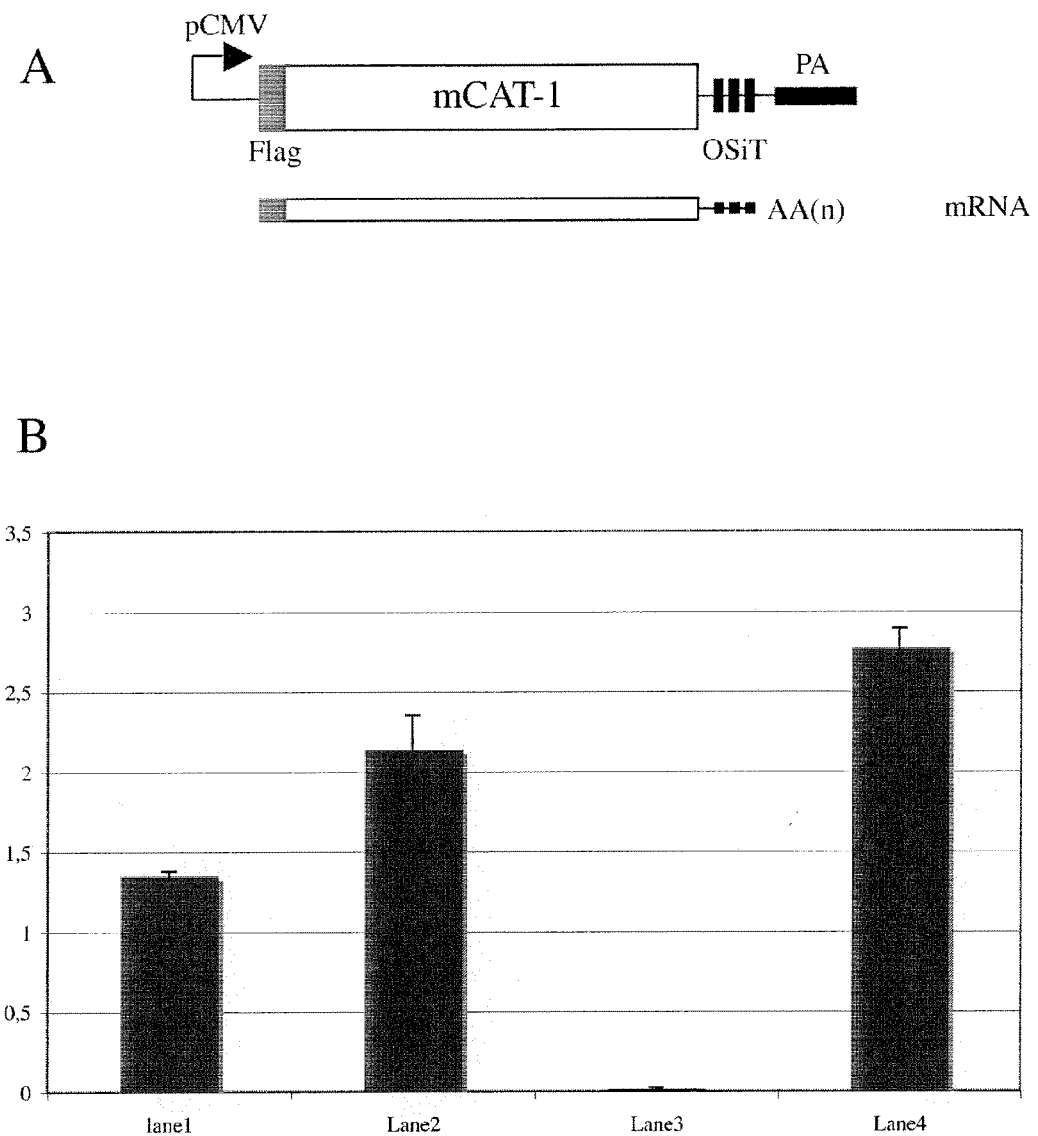

FIG. 4: EcoR Delivery in Human Cells by Ecor-Bearing Gesicles
(A) Schematic representation of mCAT-1 encoding plasmid where pCMV stands for the early human cytomegalovirus promoter, USiT for a concatemer of three repeated sequences targeted by a universal siRNA, PA for the SIV polyadenylation signal. The mRNA represented below is equipped with the USiT sequence, which renders it highly sensitive to degradation mediated by universal siRNA.

(B) Titer of GFP-encoding lentiviral vector pseudotyped with the MLV Ecotropic envelope on 293T cells treated with mCAT-1 Gesicles. HEK 293T cell were treated for 1 hour at 37° C. with 2 μg (lane 1) or 4 μg (lane 2) of concentrated Gesicles. After 2 PBS washes, cells were transduced with 100 μl of a preparation of GFP lentivectors pseudotyped with the MLV Ecotropic envelope (lanes 1, 2 and 3) or with the VSV-G envelope (lane 4). Three days after transduction, cells were analyzed by FACS and titers of vector preparation were calculated and are given as means of 3 different transduction assays.

Figure 5:
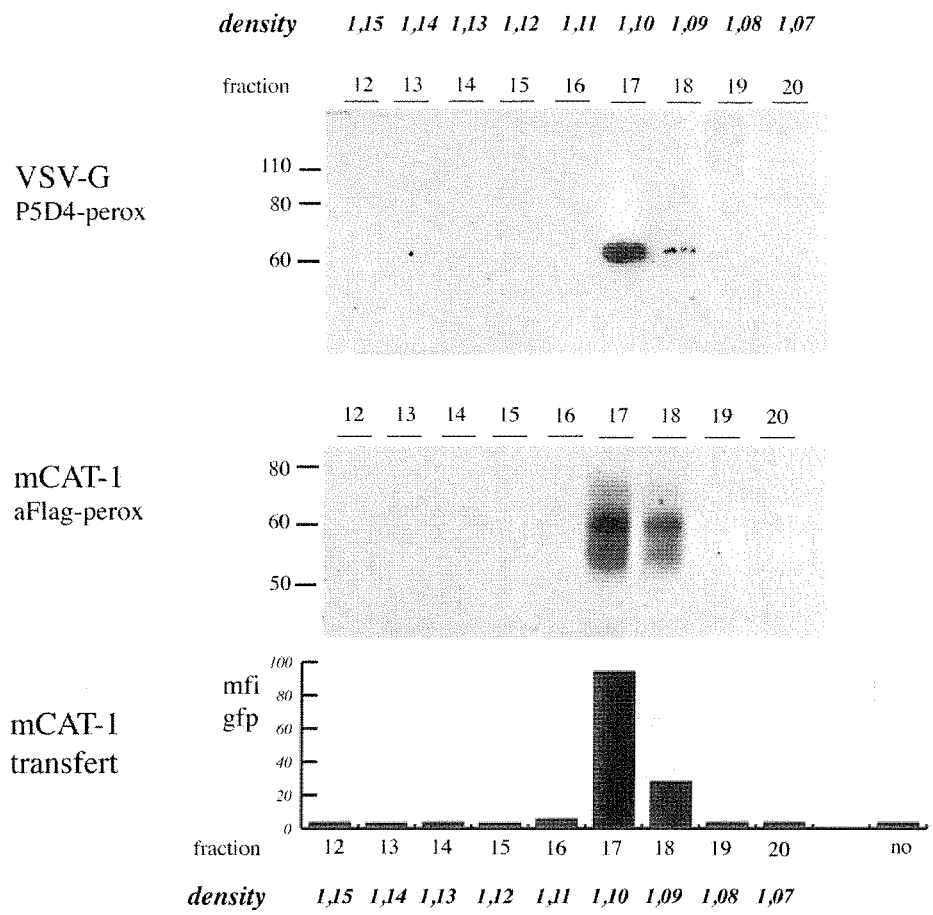

FIG. 5: Biochemical and Functional Analysis of mCAT-1 Bearing Gesicles

Gesicles were prepared upon co-transfection of HEK293T cells by VSV-G and a tagged version of mCAT-1, the receptor for the murine leukaemia virus ecotropic strain. Cell medium was changed 24 h later and collected the day after. Supernatants were clarified prior to an ultracentrifugation at 35000 rpm for 1 h30 in an SW-41 rotor. The pellet was resuspended in PBS and frozen before the density purification process.

Rate zonal centrifugation through continuous iodixanol gradients: Crude concentrated vesicles were overlaid on a continuous Optiprep gradient (6% iodixanol in 215 mM sucrose, 2 mM EDTA, 10 mM Tris HCL pH8/56.4% iodixanol in 5 mM sucrose, 2 mM EDTA, 10 mM Tris HCL pH8) and centrifuged for 12 hours at 41000 rpm in a SW41 rotor. Fractions (0.5 ml) were collected from the bottom of the gradients and kept at 4° C. before Western blot analysis and the functional assay. Density of the fractions was measured by careful weighing of 100 μl of each fraction.

Protein of fractions 12 to 20 were separated via SDS-PAGE using 4-12% Bis-Tris NuPage gels (Invitrogen) run in MOPS buffer. 5 μl of each fraction were analyzed. After electroblot onto a nitrocellulose membrane, proteins were revealed by a peroxydase-conjugated antibody directed against VSV-G (P5D4 Sigma) diluted at 1/1000 or a peroxydase-conjugated anti-Flag (Sigma) at 1/1000, both incubated one hour at room temperature.

To assess the biological activity of fractions, 30 μl of each sample were added to 293T cells seeded at 1×10e5 cells per well in a 24-well plate. One hour later medium was replaced by 200 μl of fresh medium supplemented by 200 μl of supernatant containing GFP-encoding lentivector pseudotyped with the Ecotropic envelope. 48 hours post-transduction cells were trypsinized an fluorescence values (MFI) were analyzed by FACS.

Figure 6:
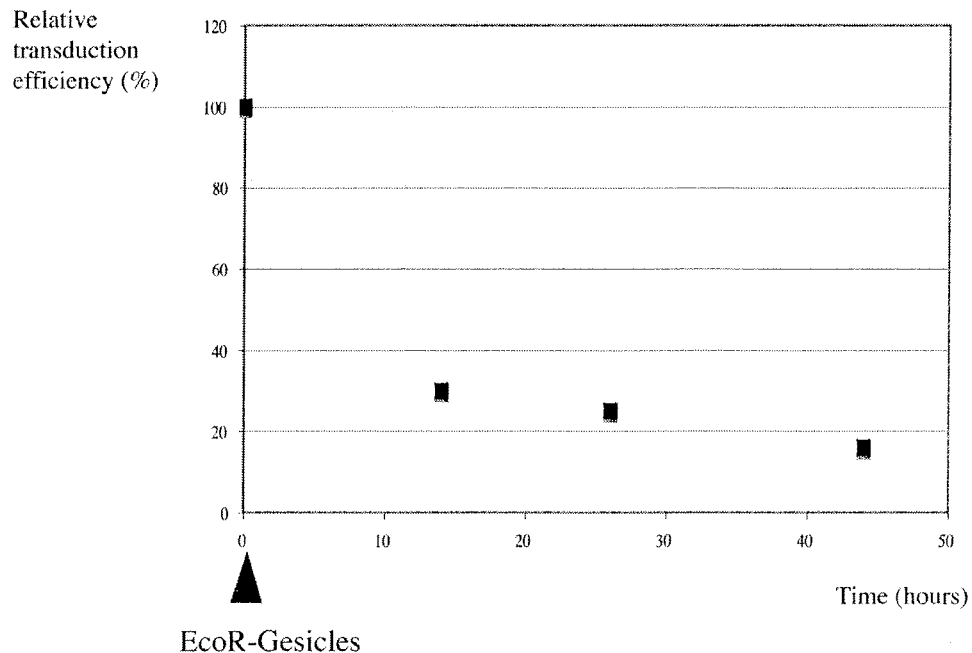

FIG. 6: Disappearance of Transferred mCAT-1 in Gesicle-Treated Human Cells

HEK293T cells were exposed to undersaturant doses of EcoR-Gesicles for 1 hour at 37°. After two washes, cells were transduced with GFP lentivectors pseudotyped with the Ecotropic envelope 5 min, 12 hours, 24 hours or 45 hours after Gesicle exposure. The same transduction assay was performed on 293T cells stably expressing EcoR to measure the progressive decrease of lentivector titer due to target cell division. Results are given as the percentage of transduction efficiency relative to the transduction value obtained at time 5 min (100%). All values were corrected in regard with the cell division rate.

Figure 7:
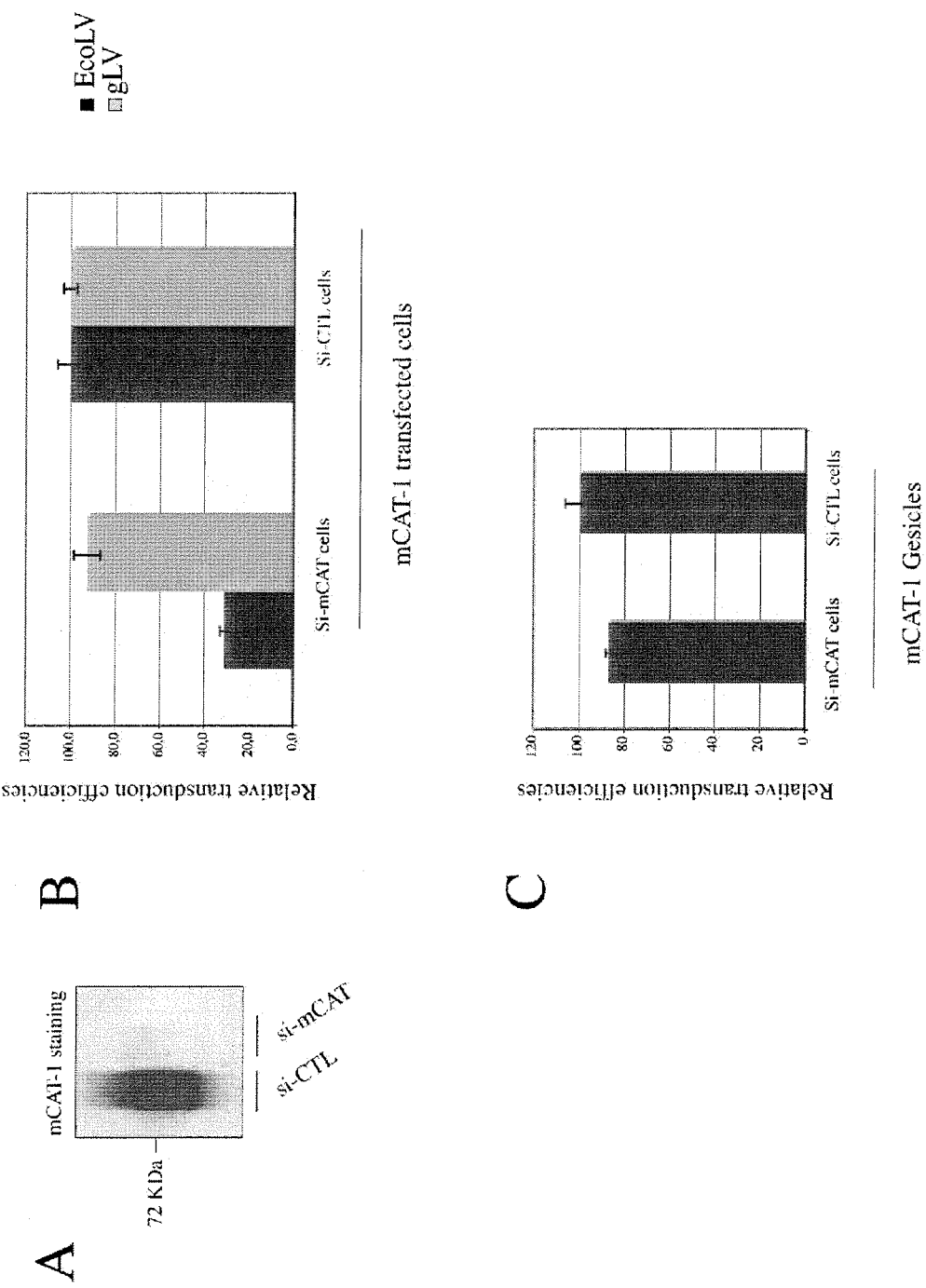

FIG. 7: Specific Degradation of EcoR mRNA does not Affect EcoR Function Introduced by Gesicles.
Functional Validation of the si-mCAT.

A synthetic siRNA designed against mCAT-1 was transfected in human cells in addition with a plasmid encoding a flagged mCAT-1. si-mCAT and si-CTL cells were next examined for their expression of mCAT and their permissiveness to transduction with Ecotropic (EcoLV) (black bars) and pantropic control lentiviral vectors (gLV) (grey bars).

(A) mCAT-1 immunostaining in si-CTL and si-mCAT cells (B) Transduction assay with GFP lentivectors in target cells transfected by mCAT-1. Transduction values were analysed by FACS 72 hours post-transduction and were set at 100% efficiency for si-CTL cells. 70% of EcoLV-transduction is inhibited in cells treated with si-mCAT while gLV-mediated transduction is almost unaffected (8% of inhibition).

Specific Degradation of the mCAT mRNA in Target Cells Hardly Affects EcoR Function Transferred by Gesicles.

(C) Transduction assay with GFP Ecotropic lentivectors in human cells treated with mCAT Gesicles. Cells treated by mCAT vesicles and bearing si-mCAT remain highly permissive to EcoLV transduction (87% of the control). This indicates that the EcoR function is mainly provided by the mCAT protein contained in microvesicles and not by contaminant mRNA nor plasmidic DNA.

Figure 8:
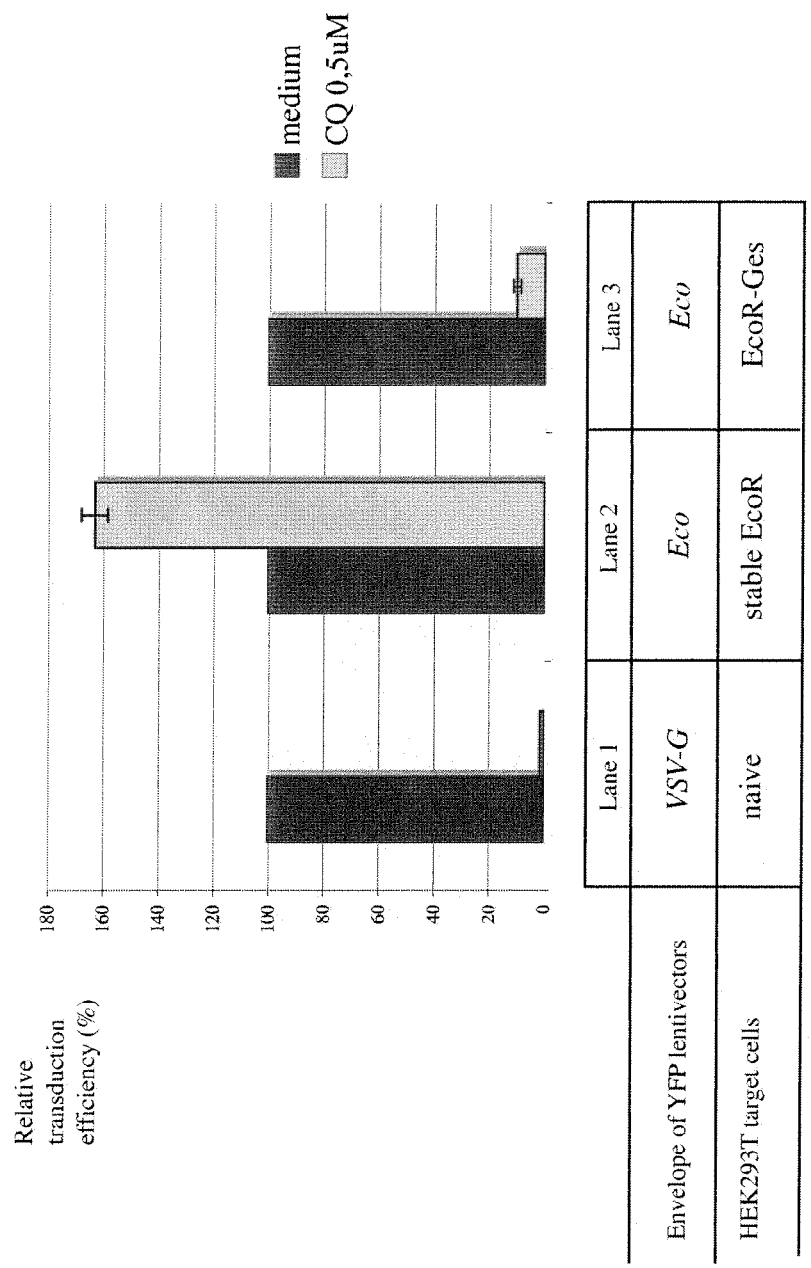

FIG. 8: Effect of Chloroquine on Ecotropic Lentiviral Transduction in Cells Modified by EcoR-Gesicles.

YFP-encoding lentiviral vectors pseudotyped with the Ecotropic envelope (Eco) were used to transducer HEK293T cells in which the mCAT-1 protein was delivered by EcoR Gesicles (EcoR-Ges) in the presence or absence of chloroquine (CQ), a drug raising the endosomal pH (lane 3). As a control, Ecotropic pseudotypes were used to transducer 293T cells in which the EcoR is stably expressed (stable EcoR, lane 2). To check the effect of CQ on endosomal acidification, VSV-G lentivectors were used to transduce target cells treated or not with the drug, illustrating the high pH-dependence of VSV-G pseudotypes (lane 1) while the ecotropic pseudotype remains efficient upon drug treatment. Results are given as the relative YFP transduction efficiency in the different cell types as measured by FACS 72 hours post-transduction.

Figure 9:
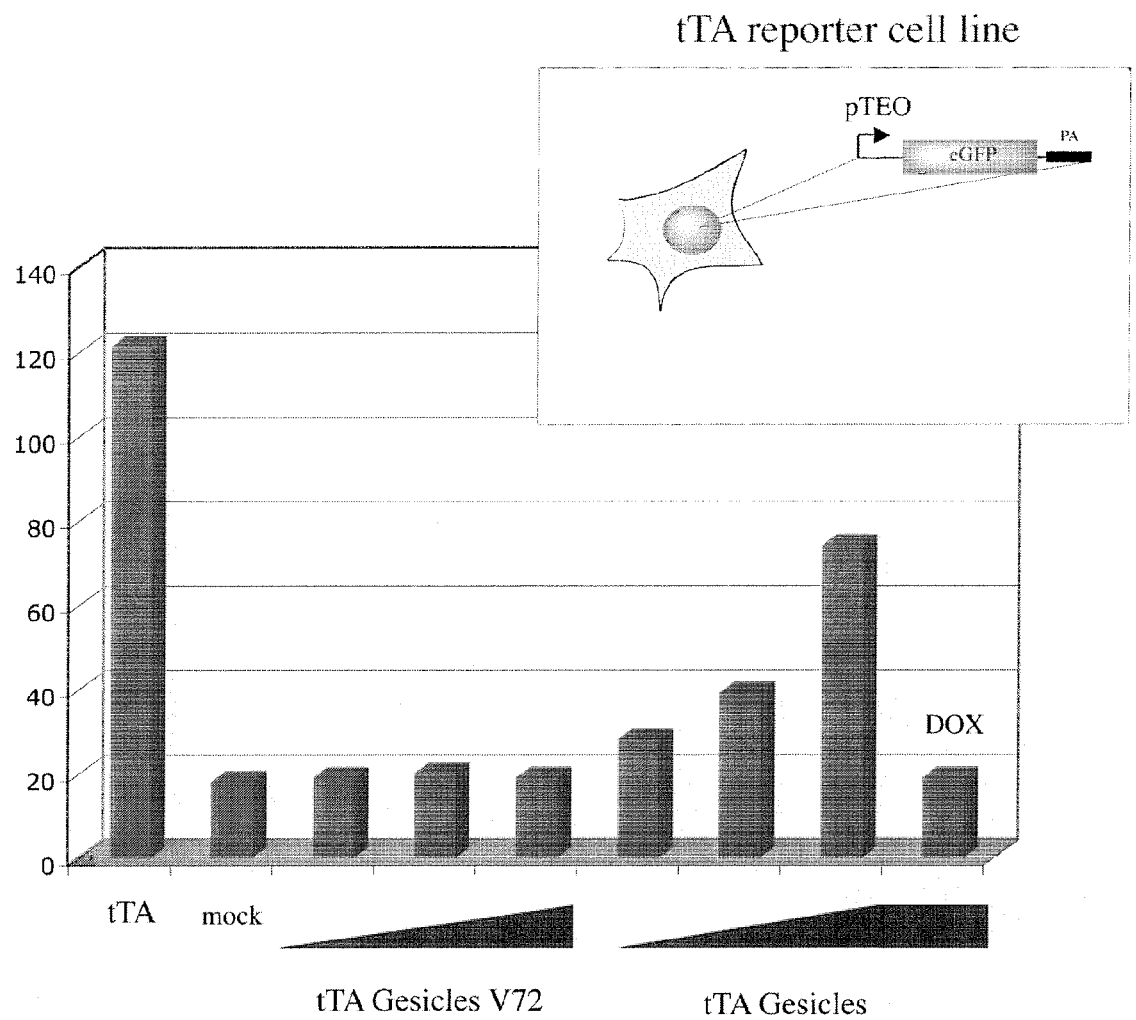

FIG. 9: Delivery of tTa by Gesicles

To detect the transcriptional function of the TET transactivating protein (tTAoff) we created a reporter cell line stably expressing eGFP under the control of the TET operator. Transfection of tTA activated the expression of eGFP in the reporter cell line (tTA lane) as compared to mock transfected cells. Gesicles produced in cells overexpressing tTA and VSV-G (wt) or its fusion incompetent mutant V72 were concentrated and laid on the reporter cell line at different doses. Increasing the dose of tTA Gesicles harbouring the wt VSV-G resulted in enhanced GFP expression. This signal could be abrogated by introduction of Doxycycline in the medium. Results are given as MFI analyzed by FACS 24 hours post-Gesicles.

Figure 10:
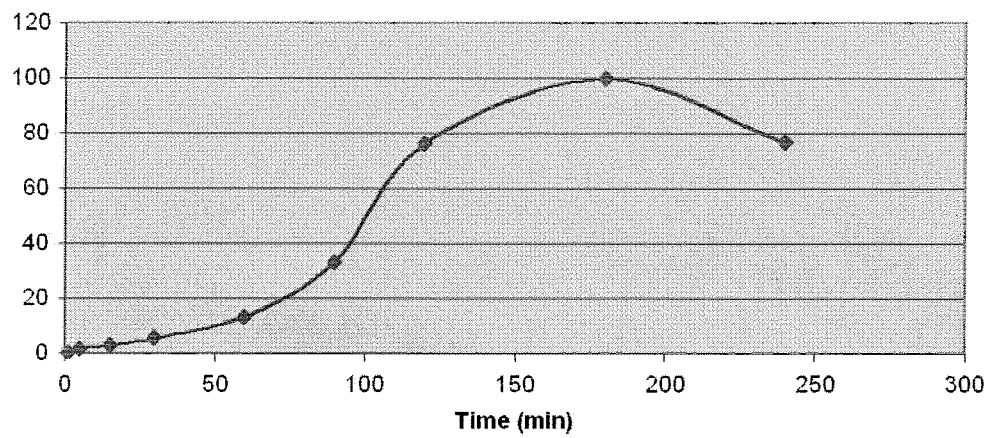

FIG. 10: Gesicle-Mediated tTa Transfer Efficiency as a Function of Time

The HEK reporter cell line Teo-GFP was plated in 12-well plates (1×10e5 cells per well) and treated with tTA Gesicles (50 μg of total protein). Exposure time ranged from 5 minutes to 4 hours. After exposure, the vesicle-containing medium was discarded and the cells washed with PBS and maintained in culture for a GFP analysis 24 hours later. tTA transfer efficiency raises gradually with time exposure up to 3 hours which is the optimal exposure time.

Figure 11:
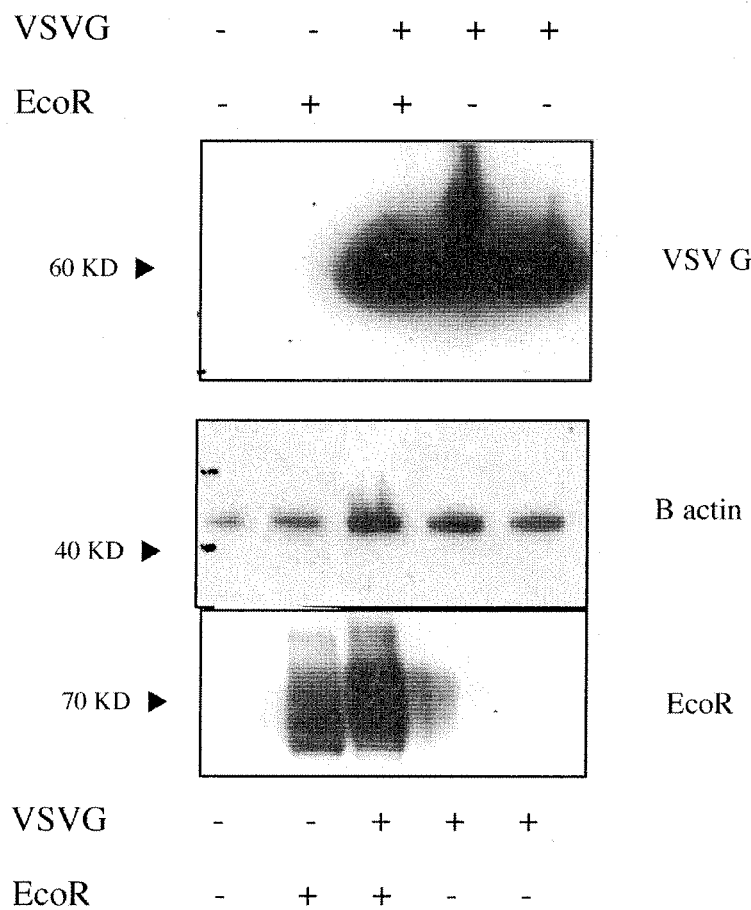

FIG. 11: VSV-G Protein Potentiates Vesicle Release and Protein of Interest Release from 293T cells Membrane Protein Release:

WB analysis of mCAT-1, a multispanning membrane protein incorporated in vesicles produced with or without VSV-G Immunolabelling of mCAT-1 in the vesicle pellet shows that mCAT-1 release is dramatically increased when VSV-G is introduced in the producer cells.

Cytoplasmic Protein Release:

A similar biochemical analysis was performed on different batches of vesicle preparations, investigating the release of the cytoplasmic protein actin. We note that VSV-G sensibly potentiates actin release as compared to mock vesicles.

Figure 12:
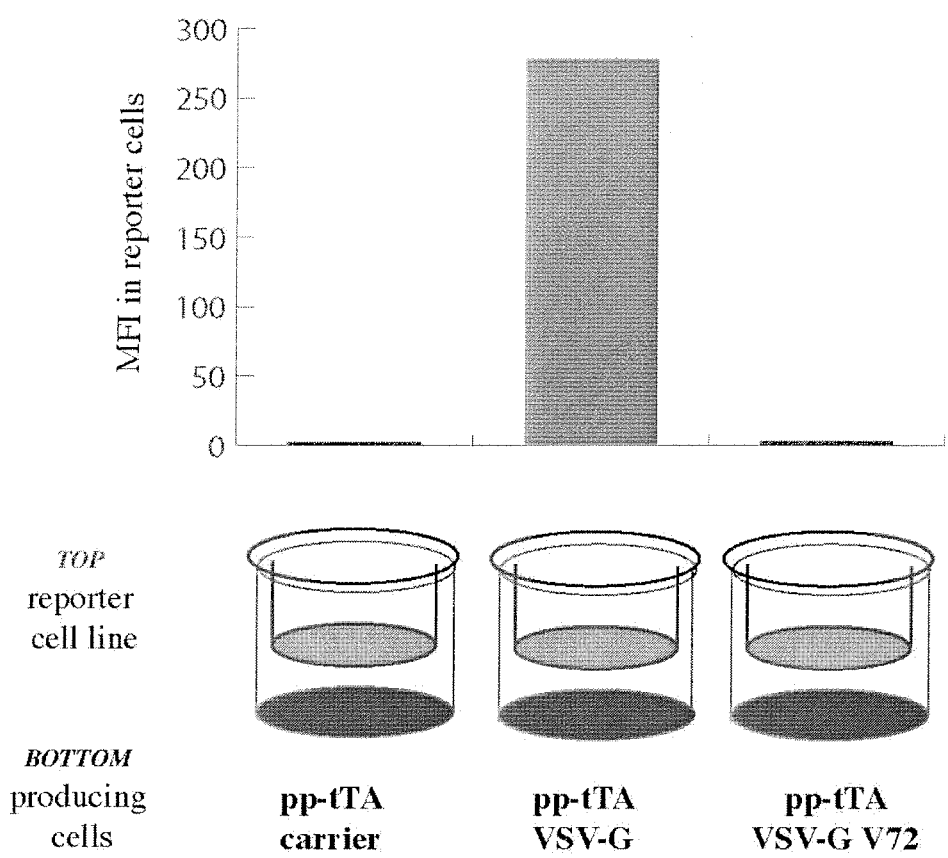

FIG. 12: Gesicle-Mediated Protein Transfer in a Co-Culture Experiment Through 3 μm-Pore Sized Inserts We cultivated in the same medium HEK cells transfected with various combinations of plasmids with the reporter Teo-GFP reporter cell line. Cells were separated by a 3 μm-pore sized filter as depicted, the producer cells in the bottom of a 6-well dish and the reporter cell line in the top insert. Producer cells were co-transfected with a tTA expression plasmid in addition with a carrier DNA, the VSV-G coding plasmid or a fusion defective VSV-G. After 48 hours of co-culture, inserts were removed and the reporter cell line trypsinized and analyzed by FACS to evaluate tTA delivery. Results are given as the MFI in the Teo-GFP cell line.

Figure 13:
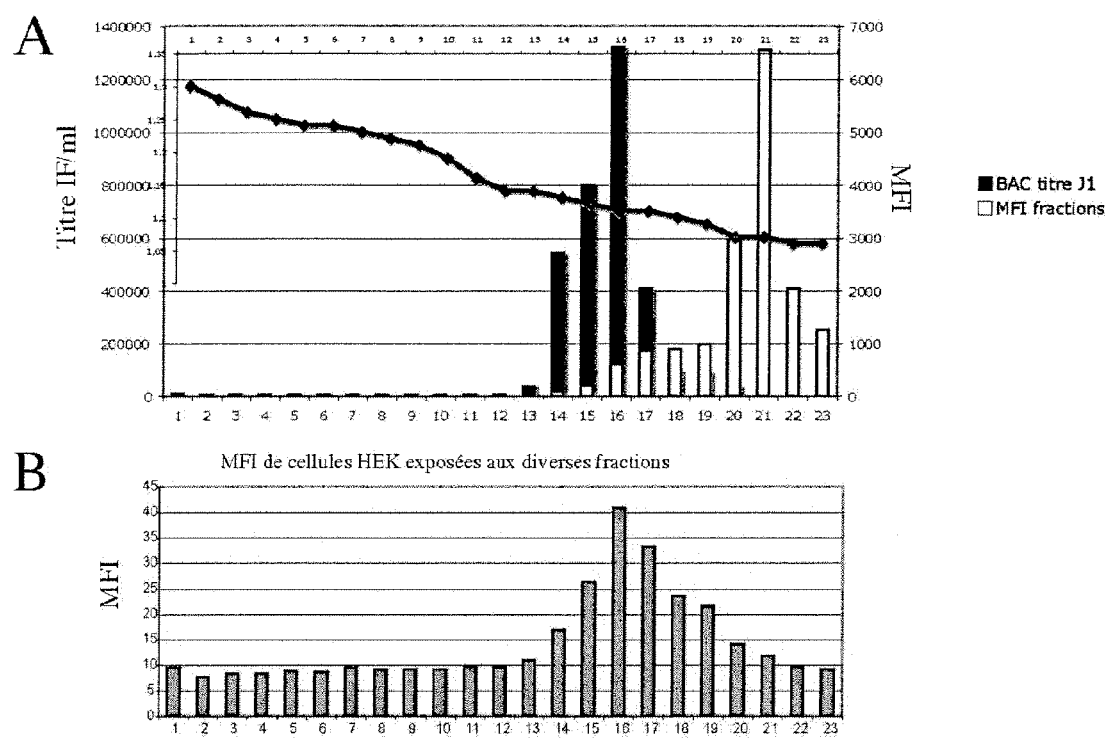

FIG. 13: Characterization of Insect Cell-Derived Microvesicles

GFP microvesicles were produced by infecting Sf9 cells for 72 hours with recombinant baculovirus. After concentration, they were laid on a iodixanol gradient and centrifuged for 10 h at 215000 g to allow sedimentation of vesicles according to their density. Fractions were collected from the bottom of the tube and their density was measured by weighing.

The density gradient can be appreciated on graph A, ranging from d=1.3 to d=1.05. All fractions were analyzed by a fluorometer to detect GFP (Exc 485 Em 515), essentially detected in fraction 21 (A, white bars). Dilutions of fractions were also used to infect sf9 cells to identify where the baculovirus sedimented. Three days after infection, sf9 cells were analyzed by FACS and Baculovirus titrated. Results given in A (black bars) indicated that the virus sedimented.

The GFP transfer capacity of each fraction was analyzed. It was contained in fractions 14 to 19, overlapping partially the virus-containing fractions.

Figure 14:
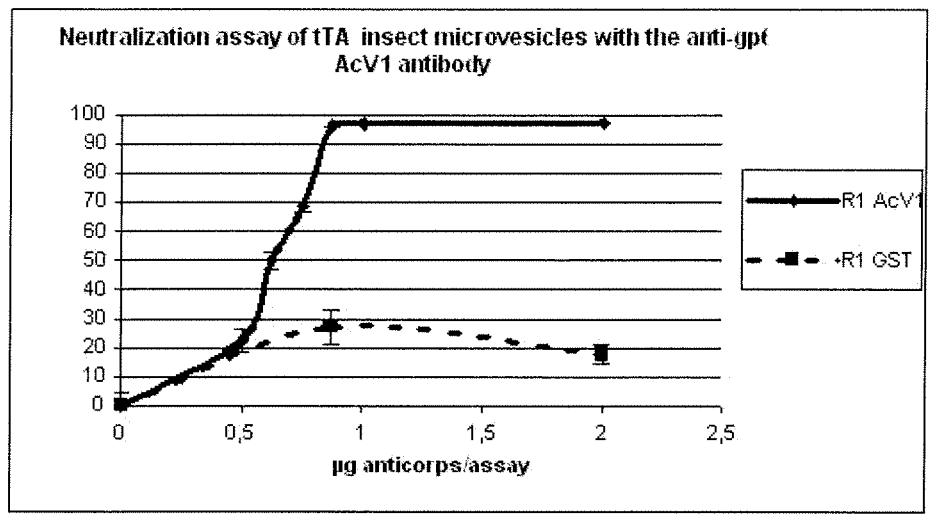

FIG. 14: Neutralization Assay (NA) of tTa Insect Microvesicles tTA microvesicles were produced in High5 cells infected with a tTA-baculovirus. Vesicles were concentrated and resuspended in PBS and diluted 10 times for the assay performed in 100 μl of PBS. 0.5 eq Phospholip tTA were incubated 2 h at 37° C. with serial dilutions of anti gp64 antibody (clone AcV1) or control antibody (GST). Vesicles were next laid on a HEK tTA reporter cell (expressing GFP once tTA is introduced in the cell). 24 hours later, vesicle-exposed cells were FACS-analysed and GFP expression was quantified. Results are given as the global population MFI.

Figure 15:
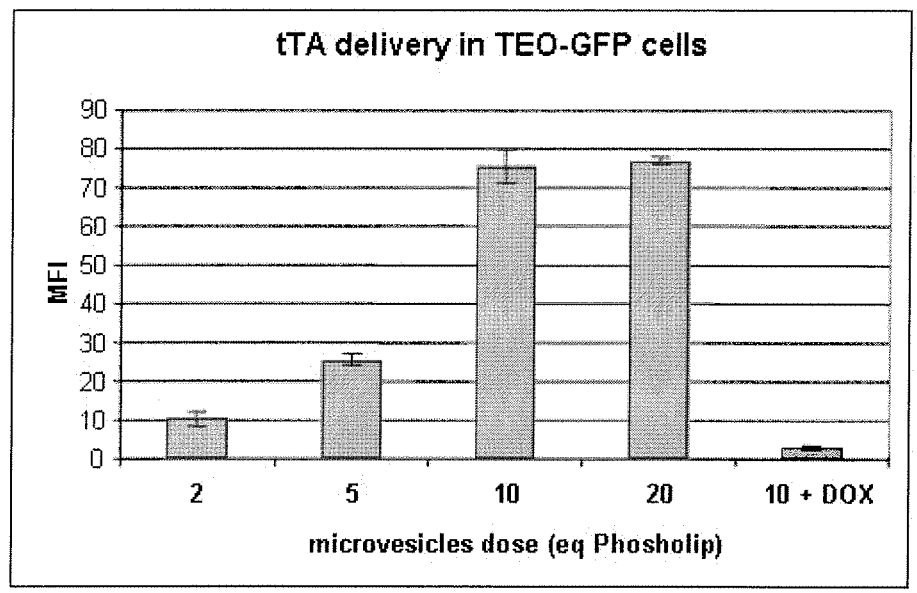

FIG. 15: Dose-Response Using tTa Microvesicles tTA insect vesicles were concentrated and purified as described prior and stored at −80°. Increasing doses of vesicles were used to deliver tTA in a HEK tTA reporter cell line, resulting in an increased GFP signal detected in target cells 24 hours post-vesicles. Doxycycline-treated cells showed background fluorescence, reflecting the expected inducibility of the TET system.

Figure 16:
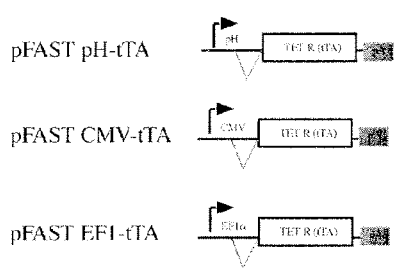
Figure 16:
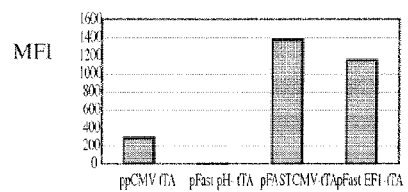
Figure 16:
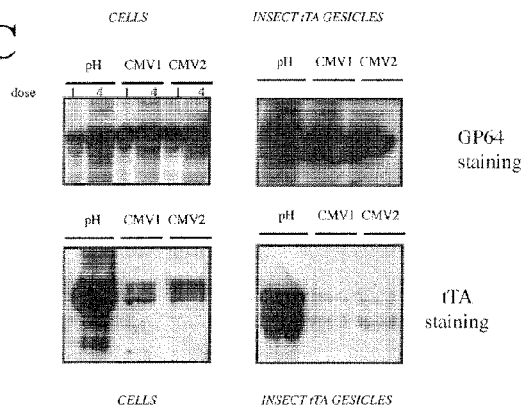
Figure 16:
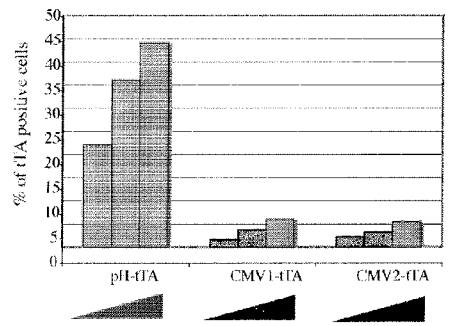

FIG. 16: Transfer of tTa in Human Cells is Achieved by Insect Cell-Derived Microvesicles and not by Coding Baculoviruses (A) Baculovirus constructs
(B) GFP expression of promoter-driven tTA in tTA reporter cell line
(C) release of GP64 and tTA into Gesicles
(D) GFP expression in the tTA reporter cell line upon treatment with pH or CMV purified microvesicles.

Figure 17:
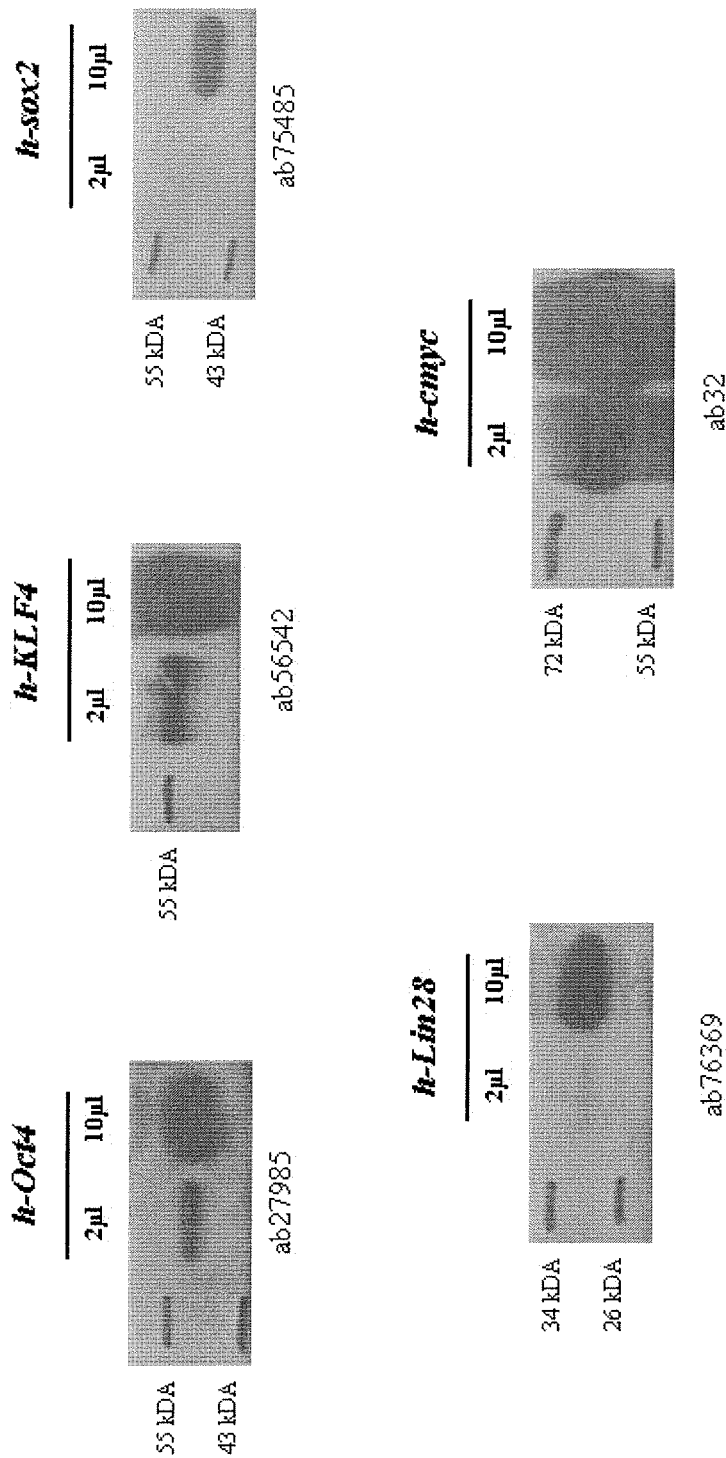

FIG. 17: Western Blot Analysis of iPS Factor-Containing Microvesicles.

Human microvesicles were prepared in HEK cells as described, lysed and analysed by SDS page. Two doses of each sample were loaded (2 μl and 10 μl of the 100× preparation corresponding to 4 μg and 20 μg of total protein amount as measured by Bradford). Immunostaining were performed using abcam antibodies (references included).

Figure 18:
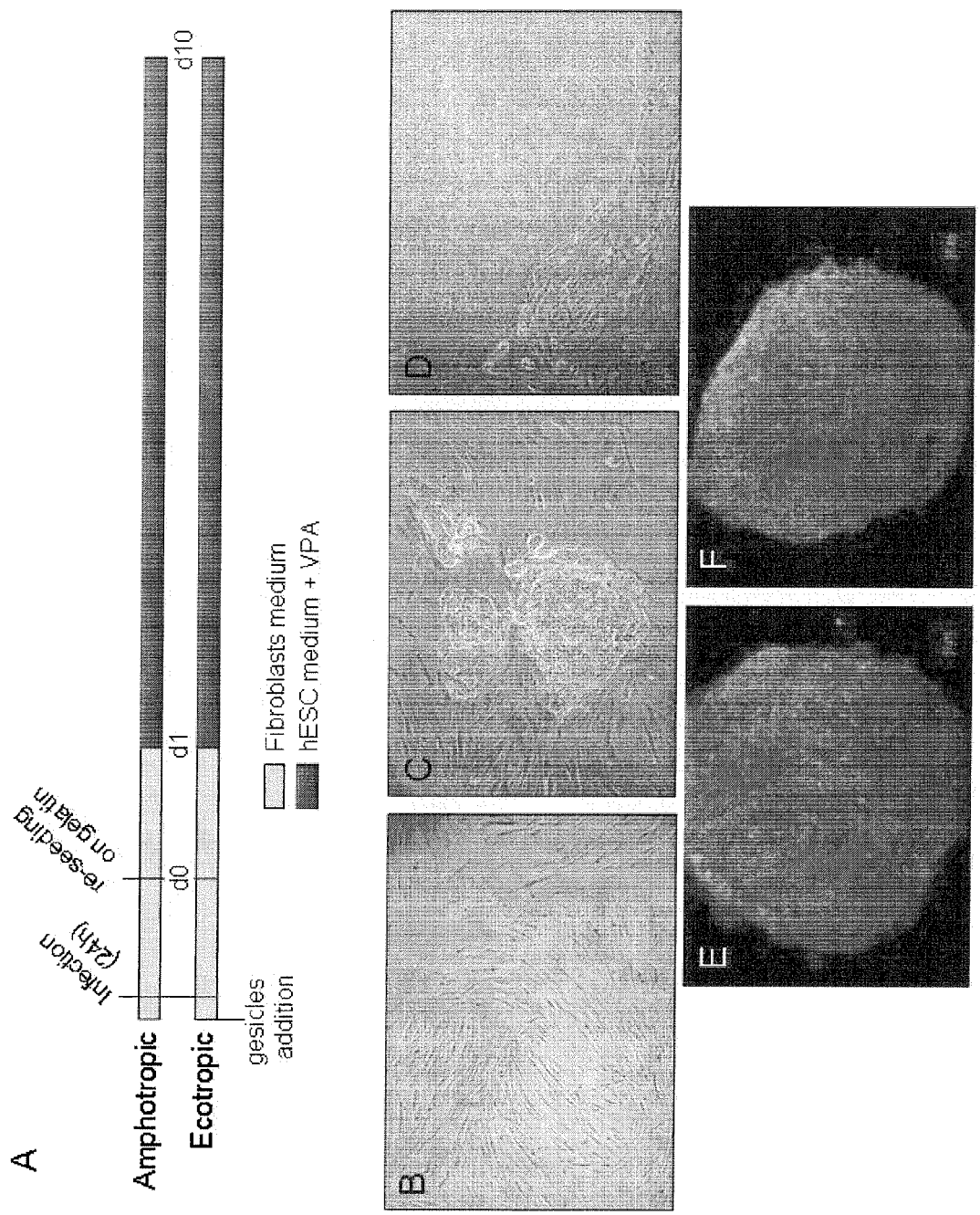

FIG. 18: Reprogramming of Fibroblasts into iPS Using EcoR Gesicles

A: Schematic representations of the amphotropic and ecotropic reprogramming protocols. In the ecotropic protocol, gesicles containing the EcoR receptor were added 1.5 hours prior to infection. In both protocols, the day cells are replated on gelatin is defined as day 0 (d0). At day 1 the medium is switched to hESC medium +VPA. The VPA treatment is maintained for 10 days, then cells are cultured in classical hESC medium until emergence of iPS clones.

B: Infected fibroblasts at day 1 (magnification ×4).
C: Emerging iPS clones at day 21 (magnification ×10).
D: Established iPS clone at passage 3 after initial picking (magnification ×10).
E: SSEA-4 immunostaining (pluripotency marker) of a clone obtained by amphotropic transduction.
F: SSEA-4 immunostaining (pluripotency) of a clone obtained by ecotropic transduction.

Figure 19:
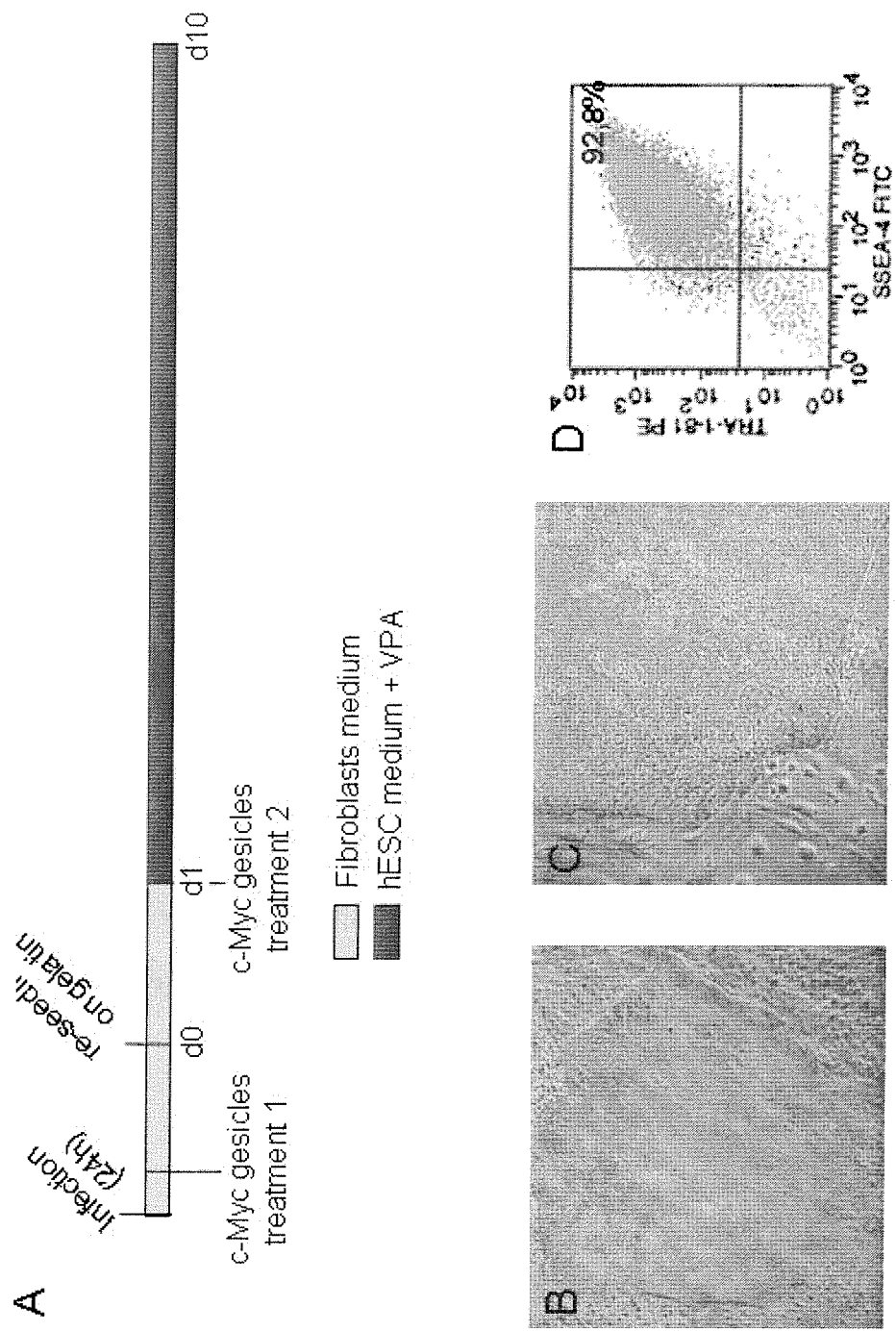

FIG. 19: Reprogramming of Fibroblasts into iPS Using C-Myc Gesicles

A: Schematic representation of the reprogramming protocol. Gesicles containing the c-Myc protein were added 6 and 36 hours after transduction by the viruses expressing the three other reprogramming factors (Oct-4, SOX2 and KLF4). The day cells are replated on gelatin is defined as day 0 (d0). At day 1 the medium was switched to hESC medium +VPA. The VPA treatment was maintained for 10 days, then cells were cultured in classical hESC medium until emergence of iPS clones. 1 clone was picked 4 weeks after transduction.

B: Established iPS clone at passage 5 after initial picking (magnification ×4)
C: Established iPS clone at passage 5 after initial picking (magnification ×10)
D: Flow cytometry analysis of iPS clone at passage 5, showing expression of un-differentiation markers SSEA-4 and TRA-1-81

EXAMPLES

Example 1

Abstract

The present example describes the engineering of exosome-like vesicles coated with the G glycoprotein of the Vesicular Stomatitis Virus (VSV-G) and used to deliver exogenous proteins in human target cells. These particles sediment at a density of 1.1 g/ml and can efficiently package cytoplasmic and membrane proteins as well as transcription factors. Model molecules including the membrane mCAT-1 protein and the tet transactivator were efficiently delivered in human target cells upon microvesicles treatment. Vesicle-mediated pseudotransduction led to transient protein expression and was not due to transfer of mRNA or DNA. We showed that chloroquine, a drug raising endosomal pH, invalidated protein transfer indicating that VSV-G induced fusion was involved in the delivery mechanism.

The Vsv-G Fusogenic Envelope is a Key Determinant of Pseudotransduction

We tested whether expression of VSV-G could lead to the production of particles able to pseudotransduce. HEK-293T cells stably expressing YFP (293T-Y) were transfected by pVSV-G, a eukaryotic expression vector. Supernatants were collected two days later, filtered and concentrated by ultracentrifugation. As a control, the same process was applied to supernatants of mock transfected 293T-Y cells. The two concentrated preparations were added on naive 293T cells, which were washed after one hour of exposure. 24 hours later, cells were trypsinized and analysed by FACS to measure the fluorescence in the two populations. We were able to observe pseudotransduction of YFP in cells exposed to the VSV-G preparation and not in cells exposed to the control preparation (FIG. 1-B). Biochemical analysis of the two samples revealed that high amounts of YFP sedimented in the VSV-G preparation (FIG. 1-A lane 1) while YFP was almost undetectable in the mock transfected preparation (lane 5). These data indicate that VSV-G is responsible for the intense release of sedimentable particles containing components of the producer cell cytoplasm. Moreover, these particles appeared to be capable of delivering this material in target cells. As cells were washed upon treatment with particles and grown during 24 hours before trypsination and analysis, we assumed that the YFP signal is intracellular and not due to fluorescent adsorbed particles at the surface of the cells. These VSV-G microvesicles will be termed as Gesicles throughout example 1.

Additional Observations:

A VSVG single amino acid mutant unable to trigger fusion (VSVG V72) 14 was tested in this system and was not incorporated in the sedimented pellet (FIG. 1 lane 2). Another western blot experiment indicated that this mutant was expressed in producer cell but not detectable in the supernatant, as opposed to the wt-VSV-G detectable in both cells and supernatant (FIG. 1C). This demonstrates that production of VSV-G microvesicles requires a fusion competent form of VSV-G in the producer cell.

Pseudotransduction of the CD81 Tetraspanin Protein

The cell-to-cell transfer of a cytoplasmic protein such as YFP by a concentrated preparation supports the idea that 293T-Y cells have produced YFP-carrying vesicles surrounded by a lipid layer and possibly coated with others proteins of 293T cells like membrane proteins. To test this hypothesis we prepared a new batch of Gesicles by transfecting 293T cells with VSV-G and use this concentrated preparation to investigate the transfer of the CD81 protein, a tetraspanin protein characteristic of exosomes and abundantly expressed on 293T cells (FIG. 2 A). The resulting material was applied on HepG2 cells, a human liver cell line lacking CD81. We showed that HepG2 cells exposed to Gesicles for one hour stained positive upon a CD81 immuno-labelling, indicating that the protein was transferred from the producer to the target cell (FIG. 2. B).

The introduction of exogenous CD81 in HepG2 is known to allow transduction of this cell line by retroviral vectors pseudotyped with the HCV envelope (HCVpp) (Zhang. et al. *Journal of virology* 78, 1448-1455 (2004)). Indeed CD81 is described as one of the HCV receptors recognized by the E2 glycoprotein. Thus to further validate the CD81 transfer, we exposed HepG2 cells to various doses of Gesicles and checked their permissiveness to HCVpp-mediated transduction as compared with naive HepG2 cells. We showed that HepG2 permissiveness to HCVpp transduction increases with the amount of Gesicles introduced in cells (FIG. 2.C), increasing HCVpp titer up to 5 fold in this experiment. This shows that the transferred CD81 protein retains its HCV binding capacity even after transport and transfer via Gesicles.

Characterization of the YFP and CD81-Carrying Gesicles

To better characterize the material responsible for protein transfer, Gesicles were produced upon transfection of VSV-G in human cells cultivated with octadecyl rhodamine B chloride (R18), a lipophilic fluorophore labelling the membranes. After a first concentration step, R18-Gesicles were laid on a continuous iodixanol gradient and centrifuged 3 hours to allow separation of fractions according to their density. All collected fractions from 1 to 20 were analysed for their capacity to emit fluorescence at 590 nm after excitation at 560 nm, the emission and excitation values for R18. As shown in FIG. 3A, R18-fluorescence is detected in fractions 13 to 20 with a peak in fraction 17 which corresponds to a density of 1.11 g/ml.

In another experiment, Gesicles produced in 293T-Y were similarly processed and laid on a gradient prior analysis of YFP-associated fluorescence in the different collected fractions. FIG. 3B indicates that YFP was principally detected in fractions 17 and 18 corresponding to densities of 1.10-1.11. We next examined which fraction was able to deliver YFP by pseudotransduction. ⅒ of each sample was applied on 293T cells and fluorescence transfers were FACS-analysed 24 hours later. As shown in FIG. 3, the pseudotransduction determinant was essentially sedimented in fraction 17 (d=1.11). In another experiment, Gesicles were separated and analysed by Western blot. Analysis of density-fractions revealed that VSV-G and CD81 were clearly enriched in fractions 17 and 18 which correspond to densities of 1.10 and 1.11 g/ml (FIG. 2D). As the CD81 molecule is described as a marker for exosomes (Lamparski et al. *Journal of immunological methods* 270, 211-226 (2002)) we can conclude that VSV-G-carrying Gesicles are a particular type of exosome-like vesicles.

Combined, our findings indicate that upon VSV-G transfection, HEK 293T cells produced membrane-surrounded Gesicles sedimentable at a density of 1.10-1.11 g/ml and that these exosome-like microvesicles contain proteins such as CD81 from the producer cells that are deliverable in target cells.

Gesicles-Mediated Transfer of mCAT-1 in Human Cells.

In the same manner as YFP or highly-expressed CD81 are packaged in Gesicles produced by 293T-Y/293T cells, we tested whether any protein overexpressed in the producer cell could be passively incorporated in nascent Gesicles and whether low amounts of this packaged material could be delivered in human target cells. This notion was tested using the mCAT-1 protein as a model, the murine cationic amino acid transporter also known as the receptor for the murine leukemia virus (MLV) Ecotropic envelope EcoR. A plasmid encoding a flagged version of mCAT-1 was constructed (SwFlag EcoR depicted at FIG. 4) and cotransfected with VSV-G in 293T-Y cells to produce EcoR-bearing concentrated Gesicles subsequently introduced on human cells. After one hour, exposed cells were washed and stained positive for EcoR expression as revealed by a FACS analysis using an anti Flag-FITC antibody (not shown). To further validate the mCAT-1 transfer, we developed a transduction assay based on YFP-encoding lentivectors pseudotyped with the MLV-Ecotropic envelope. Due to the particular tropism of this glycoprotein, these lentivectors can transduce exclusively murine/rat cells or human cells in which mCAT-1 is expressed upon transfection. If EcoR-Gesicles efficiently deliver EcoR in human cells, these should become permissive to an Ecotropic YFP lentitransduction.

Results shown FIG. 4 give the titers of an Ecotropic lentivector preparation upon titration on human cells treated or not with EcoR Gesicles. While naive cells are restrictive to transduction with an Ecotropic lentivector (lane 3), cells treated with 2 μg (lane 1) or 4 μg (lane 2) of concentrated Gesicles become highly permissive to Ecotropic transduction. To avoid incorporation of Gesicles-G protein on Ecotropic lentivectors in the transduction medium, Gesicle-treated cells were washed twice prior transduction.

EcoR-Gesicles preparation was laid on a density gradient as previously described to identify the fraction responsible for the transfer of mCAT-1. Collected fractions were analysed by western blot and for their capacity to mediate EcoR transfer (FIG. 5). In this experiment, we show that fraction 17 corresponding to a density of 1.10 is highly enriched in VSV-G and mCAT-1 and is the main fraction responsible for EcoR transfer as revealed by a transduction assay. These data indicate that EcoR-Gesicles sedimenting at a density of 1.10 transferred the mCAT-1 protein in the membrane of target cells where it retains its binding property for the ecotropic envelope.

Moreover we show here that Gesicle content, and particularly the nature of proteins borne by the membrane of Gesicles can be easily controlled by transfection of producer cells.

Mechanistic of EcoR-Delivery by Gesicles
Lifetime of Transferred mCAT-1

We next examine the lifetime of the transferred mCAT-1 in human cells by varying the delay between the Gesicles exposure and the transduction assay. Results shown in FIG. 6 indicate that Eco receptor function disappeared from the 293T-cell surface around 50 hours after its Gesicle-mediated transfer. This experiment was reproduced on different human cell types including Hela, HUH.7 (not shown) without modification of the half-life of transferred mCAT-1 close to 24 hours. This transience comforts the notion that Gesicles deliver proteins and not plasmidic DNA that could contaminate the Gesicles preparation. Indeed encoding of mCAT-1 by plasmidic DNA would necessitate a transcription and a translation step in the target cells, leading to an expression peak 48 h after introduction as it is commonly observed for transfection experiments.

The EcoR Function is Provided by Ready-Made Proteins Incorporated in Gesicles.

To investigate the nature of the material transferred with the mCAT-1 vesicles, we treated human target cells with a siRNA directed against the mCAT-1 mRNA. Should the vesicles deliver mRNA or DNA encoding it, it would be rapidly degraded in si-mCAT treated cells.

As revealed by a mCAT-1 immunostaining (FIG. 7A), the mCAT-1 siRNA suppressed mCAT expression upon a cotransfection experiment in HEK cells. Moreover, introduction of this specific siRNA in cells transfected with a mCAT-1 plasmid strongly decreased the capacity of cells to be transduced with ecotropic lentivectors (FIG. 7B). While VSV-G pseudotyped lentivectors (gLV) transduced efficiently both si-CTL and si-mCAT cells, the transduction efficiency achieved with ecotropic lentivectors (EcoLV) was inhibited in si-mCAT cells (70% of inhibition). These data indicate that the si-mCAT impacts specifically on the mCAT-1 receptor function when this is coded by a plasmid.

We next examined whether the mCAT-siRNA affected the receptor function delivered by mCAT-1 microvesicles. Cells were transfected with mCAT and control siRNAs and treated with mCAT-1 vesicles 48 hours later. A transduction assay was next performed with EcoLV to check the receptor function (FIG. 7C). Both si-CTL and si-mCAT cells were efficiently transduced with EcoLV, indicating that the si-mCAT largely failed in suppressing the receptor function delivered by vesicles. This indicates that microvesicles essentially delivered the receptor function by transferring ready-made proteins and not mRNA or contaminating plasmid DNA.

Gesicle-Mediated EcoR Delivery is pH-Dependent

Since the transferred EcoR protein is functional as a viral receptor, this implies its presence at the surface of the target cell. However, due to the nature of the VSV-G envelope, fusion between Gesicles and cell membrane is expected to take place in the internal acidic compartments, liberating the EcoR protein inside the cell and not at the surface where it is functional.

To gain insights in the mechanism of EcoR-transfer, we treated 239T target cells with chloroquine (CQ) before Gesicles treatment, a drug raising endosomal-pH and known to disrupt membrane fusion triggered by VSV-G. As shown in FIG. 8, VSV-G-pseudotyped lentivectors are unable to transduce CQ-treated cells (lane 1) while Ecotropic lentivectors remain efficient when used on drugged-293T expressing constitutively mCAT-1 (lane 2). These data illustrate the pH-dependence. Interestingly we show that CQ strongly inhibits EcoR-delivery by gesicles (lane 3). Since transduction with ecotropic reporter lentivectors is not decreased by CQ, this result reflects a CQ-mediated failure in the cell mechanism delivering EcoR at the surface.

Considering these data, we propose a model where Gesicles after being internalized in the target cell are transported in the endosomal compartments where fusion of membranes is required for EcoR release. The proteins, following the fate of many endogenous receptors, would be subsequently recycled toward the cell membrane.

Gesicle-Mediated Delivery of the TET Transactivator

Besides delivery of cytoplasmic and membrane proteins, we explored the capacity of Gesicles to package and deliver transcription factors, proteins classically expressed in the nucleus. For this purpose Gesicles were produced in 293T cells cotransfected with a plasmid encoding the TEToff transactivator (tTA), a synthetic transcription factor activating transcription of its cognate promoter the Tet operator (TEO) and that can be switched-off by introduction of tetracycline/doxycycline in the cell culture medium (Gossen et al., *Proceedings of the National Academy of Sciences of the United States of America* 89, 5547-5551 (1992)). Increasing doses of tTA loaded gesicles were next laid on reporter cells harbouring an expression cassette composed of the eGFP gene under the control of the Tet operator. Result shown in FIG. 9 indicate that fluorescence of the reporter cell line is activated by tTA Gesicles 24 hours after treatment. Fluorescence signal increases with gesicle-doses and reaches for the highest dose around 50% of the signal obtained in a reporter cells transfected with a tTA construct. We note that transcription activation in the treated cells remains sensible to Doxycycline treatment. This indicates that the tet transactivator protein has been successfully packaged in Gesicles and transferred in the reporter cell line.

Gesicle Mediated tTA Transfer Efficiency as a Function of Exposure Time

The HEK reporter cell line Teo-GFP was plated in 12well plate ($10^5$ cells) and treated with tTA gesicles (50 μg of total protein per well). Exposure time ranged from 5 minutes to 4 hours. After exposure, vesicle-containing medium was discarded, cells were washed with PBS and maintained in culture for a GFP analysis 24 hours later. tTA transfer efficiency raises gradually with time exposure up to 3 hours which is the optimal exposure time (see FIG. 10).

Gesicles Production and Dosage Methods

Human EcoR-Gesicles Production and Dosage

Human gesicles were produced by transfection of HEK 293T cells using the calcium phosphate method. Cells were seeded at $3 \times 10^6$ cells in 10 cm dishes and cotransfected with 12 µg of a VSV-G encoding plasmid and 12 µg of the mCAT-1 encoding plasmid per dish. Transfection medium was changed 24 h latter and vesicles-containing supernatant were collected 48 hours and 72 hours after transfection, pooled, filtered through a 0.45 um filter, and ultracentrifuged 1H30 in a SW41 rotor at 25000 rpm (110000 g). Pelleted material was finally resuspended in cold PBS resulting in a 200-fold concentration. Large preparations were performed using six 10-cm dishes and generated around 400 µl of 200× vesicles.

YFP/CD81 carrying vesicles were produced by transfecting 14 µg of VSV-G plasmid in HEK-293T cells previously transduced by a YFP-expressing lentivector.

To quantify the amount of proteins in sedimented microvesicles, we developed an ELISAssay detecting the flagged mCAT-1 protein. Briefly, serial dilutions of vesicles were lysed in PBS/Triton X100 2% and coated overnight in a 96-well plate (NUNC.Maxisorp) in a carbonate coating buffer (pH 9.6). Serial dilutions of the flag-peptide (Sigma) were coated in parallel in a Triton-free buffer. Proteins and peptide were revealed upon 1 h-incubation of the washed plate with an anti-Flag-HRP antibody diluted at 1/1000 (M2 Sigma) and a final revelation with the TMB substrate. These assays allowed us to dose the amount of flagged-protein in the vesicle-preparation.

Alternatively, we engineered a VSV-G Elisa assay by coating serial dilutions of the VSV-G peptide recognized by the anti-VSVG antibody coupled with HRP (P5D4. Sigma). Thus all VSV-G vesicles can be expressed as an equivalent mass of VSV-G peptide per microliter of the vesicle preparation.

Discussion

We developed here an original and simple way to transfer cytoplasmic and membrane proteins in human cells by the use of engineered exosome-like vesicles. This Gesicle-mediated protein delivery technology was further used to introduce a functional transcription factor in human cells. Production of these microvesicles was achieved by overexpression of the protein of interest in 293T producer cells cotransfected with VSV-G. VSV-G appears to boost vesicles production from 293T cells as revealed by the analysis of supernatants enriched in membrane proteins as well as membrane lipids and actin (FIG. 11). Furthermore, by coating the membranes of microvesicles, the fusogenic G protein enhances their ability to contact target cells and allows very efficient fusion between particles and cell membranes, a prerequisite for the release of the microvesicle content in the target cells.

Example 2

Vesicle-Mediated Protein Transfer in a Coculture Experiment Through 3-µm Pore Sized Inserts We cultivated in the same media HEK cells transfected by various combinations of plasmids, together with the Teo-GFP reporter cell line. Cells were separated by a 3-µm pore sized filter as depicted, the producing cells in the bottom of a 6-well dish and the reporter cell line in the top insert. Producing cells were cotransfected with a tTA expression plasmid in addition with a carrier DNA, the VSV-G coding plasmid or a fusion defective VSV-G. After 48 hours of coculture, inserts were removed and the reporter cell line trypsinized and analysed by FACS to evaluate tTA delivery. Results are given as the MFI in the Teo-GFP cell line (FIG. 12).

This technique enables the delivery of protein into target cells, without the need of a concentration step. Concentrated vesicles can be toxic depending on the target cell type. Target cells can be cultivated in the top or the bottom chamber and infused several days with vesicles producing-cells for a constant protein delivery. Successive infusions can even be performed if several factors have to be introduced sequentially by easy transfer of the insert in another vesicle-containing bath.

Example 3

Insect Cells Microvesicle Production and Dosage

Baculovirus production was performed using the Bac-to-Bac Baculovirus expression system (Invitrogen) according to the manufacturer's instructions. Briefly, cDNAs of interest were cloned in the pFAST-1 shuttle prior to recombination in DH10-BAC bacteria. Baculovirus DNAs were next used to transfect SF-9 cells to generate the first baculo stock collected 72 hours later (passage 1). This polyclonal stock was further amplified to reach a titer of $1 \times 10^7$ pfu/ml (passage 2) that was stored at 4° C. and used for vesicles production.

Insect cells microvesicles were produced upon baculovirus infection (MOI 0.5-1) of $200 \times 10^6$ HIGH5 cells cultivated in suspension at 30° C. under agitation in 100 ml of Express-five SFM media supplemented with Glutamine (20 mM) and Penicillin-Streptomycin (25 U of penicillin, 25 µg of Streptomycin/ml). 48 hours after inoculation, medium was harvested clarified and filtered twice through a 0.45 µm pore-sized filter prior to ultracentrifugation in a SW-32 rotor at 24000 rpm (100.000 g). Sedimented material was next resuspended in cold PBS (100× concentration) and stored at −80° C.

For a better purification, this cloudy preparation was laid on a discontinuous iodixanol gradient to allow separation of discrete density fractions. Biological analysis of fractions revealed that active vesicles able to transfer harboured proteins sedimented at a density between 1.09-1.11. Highly purified vesicles were prepared upon pooling these fractions and after a last concentration step of the pool supplemented with cold PBS (1 h at 30000 rpm in SW41).

Insect cell-derived vesicles were quantified with the phospholipid-enzymatic PAP50 detection kit (Biomérieux) and with the VSV-G ELISA described above.

Characterization of Insect Cell Derived Microvesicles

GFP microvesicles were produced as described upon infection of sf9 cells for 72 h with a recombinant baculovirus. After concentration, vesicles were laid on an iodixanol gradient and centrifuged at 215000 g for 10 h to allow sedimentation of vesicles according to their density. Fractions were next collected from the bottom of the tube and their density was measured by weighing. The density gradient can be appreciated on the graph of the FIG. 13A, ranging from d=1.3 to 1.05. All fractions were analysed by a fluorometer to detect GFP (Exc 485 Em 515) essentially detected in fraction 21 (FIG. 13A white bars). Dilutions of fractions were also used to infect sf9 cells to identify where the GFP Baculovirus sedimented. Three days after infection, sf9 were analysed by FACS and the Baculovirus titer was calculated. Results given in A (black bars) indicated that the virus sedimented between fraction 13 and fraction 20 with a peak for fraction 16. We also used the fractions to deliver GFP in human cells and analysed fluorescence transfer 24 h latter (FIG. 13B). Interestingly, we found that the GFP transfer capacity was contained in fractions 14 to 19, overlapping in part the virus containing fractions.

Neutralization Assay (NA) of tTA Insect Microvesicles.

tTA microvesicles were produced in High5 cells infected with a tTA-baculovirus. Vesicles were concentrated and resuspended in PBS and diluted 10 times for the assay performed in 100 µl of PBS. 0.5 eq Phospholip tTA were incubated 2 hours at 37° C. with serial dilutions of anti gp64 antibody (clone AcV1) or control antibody. Vesicles were next laid on a HEK tTA reporter cell (expressing GFP once tTA is introduced in the cell). 24 hours later, vesicle-exposed cells were FACS-analysed and GFP expression was quantified. Results (see FIG. 14) are given as the global population MFI.

Dose Response Using tTA Insect Microvesicles.

tTA insect microvesicles were concentrated and purified as described previously and stored at −80° C. Increasing doses of vesicles were used to deliver tTA in a HEK tTA reporter cell line, resulting in an increasing GFP signal detected in target cells 24 hours post-vesicles. Doxycycline-treated cells showed background fluorescence, reflecting the expected induciblity of the TET system (see FIG. 15).

Discussion

We have shown that production of human cell derived vesicles was achieved upon cotransfection of producer cells with the VSV-G coding plasmid and another plasmid encoding the protein of interest (YFP, mCAT-1, tTA . . . ). To increase the performance of the production system, we constructed recombinant baculoviruses encoding VSV-G and tTA and infected insect cells highly permissive to baculovirus infection. Moreover High5 cells and SF9 cells can be cultivated easily in suspension up to $2 \times 10^6$/ml without serum or even in synthetic media devoid of animal product. Notably, baculoviruses do not replicate in human cells and the polyhedrin promoter driving expression of the transgene is insect cell specific and not active in human cells.

We found that upon coinfection with tTA and VSVG, insect cells produced microvesicles able to transfer tTA in human cells. We also found that VSV-G was useful but dispensable in this process, suggesting that another fusion protein could replace it. This role could be assumed by gp64, the envelope glycoprotein of Baculovirus that is expressed in all infected cells. By performing a neutralization assay, we have shown that protein delivery mediated by insect microvesicles could be neutralized by a gp64 antibody.

To further characterize insect cell vesicles, we laid GFP insect-vesicles on an iodixanol gradient to measure their density. This process allows separation of different materials present in a mixture according to their respective density. This experiment indicated that the vesicle-containing fraction was overlapping with the baculovirus-containing fractions. It is commonly admitted that baculovirus cannot replicate in human cells, however we can imagine that a slight expression of tTA coding baculoviruses could produce enough tTA to activate the GFP expression in the reporter target cells. To check this, we replaced the insect specific polyhedrin promoter (pH) by the CMV or the EFIa promoter in the shuttle plasmid (pFAST) used to construct the Bac recombinant (constructs depicted in FIG. 16A). As opposed to pH, those promoters are highly active in human cells as revealed by a transfection experiment in the HEK-Teo GFP reporter cell line (FIG. 16B). We next chose the CMV promoter to generate two recombinant baculoviruses (CMV1 and CMV2) subsequently amplified and used to infect in sf9 cells. Both CMV recombinants infected sf9 cells as efficiently as the pH recombinant. This was revealed by a western blot analysis performed on producer cells lysates (FIG. 16C). The baculovirus protein gp64 was clearly detected in cell lysates regardless the nature of the promoter used. Upon microvesicles preparation, we performed the same staining on microvesicle lysates and verified that gp64 was highly detected in the three samples, showing that the CMV replacement did not significantly affect neither baculovirus infection in sf9 nor virus-release. As expected, we found that the pH recombinant expressed higher levels of tTA in sf9 cells as compared with the two CMV recombinants. This logically impacted the tTA amount detected in microvesicles, considerably higher in the pH lysates. Increasing doses of pH-tTA and CMV-tTA microvesicles were finally laid on the HEK-TeoGFP cell line. MFI reflecting the efficacy of tTA delivery was analysed by FACS 24 h later revealing that the vesicles produced with the pH recombinant were ten-fold more efficient than those produced with the CMV recombinants (FIG. 16D). This shows that an efficient tTA transfer correlates with high levels of protein expression in the producer cells. This supports the hypothesis that the protein itself is transmitted by baculovirus associated microvesicles. Moreover, increasing the transcription performance of the tTA baculovirus in the human cell by promoter swapping does not increase tTA availability in the target, showing that Baculovirus-driven transcription is not responsible (or poorly involved) of the delivered tTA function. Altogether these data show that transfer of tTA in human cells is achieved by insect-cell derived gp64 microvesicles and not by coding baculoviruses.

Example 4

Gesicles can be Used for Reprogramming Cells and Producing Induced Pluripotent Stem Cells (iPS)

Example 4A

Reprogramming Using Gesicles Containing EcoR

Cell Culture

Human normal adult fibroblasts (ordered from Coriell cell repository) were maintained in DMEM high Glucose supplemented with 10% FBS, 1 mM sodium pyruvate and 2 mM GlutaMA™. Human iPS cells were maintained on mytomycin-C growth-arrested MEF feeder cells in human ES cell medium, i.e. Knockout DMEM supplemented with 20% knockout serum replacement, 10 ng/ml bFGF, 0.1 mM nonessential amino acids, 50 mM (3-mercaptoethanol, 2 mM GlutaMA™ and 0.1% penicillin/streptomycin.

Retrovirus Production

Moloney-based retroviral vectors (pMIGs) containing human complementary DNAs (cDNAs) of c-Myc, Oct4, Sox2 and Klf4 were obtained from Addgene. These plasmids were individually transfected using FuGene into PLAT-A (for amphotropic viral production) or PLAT-E (for ecotropic viral production) packaging cells. PLAT cells medium was replaced 24 h post-transfection. Viral supernatants were collected 48 h post-transfection, filtered through a 0.45µ filter, then mixed at a 1:1:1:1 ratio.

Production of Gesicles Containing the Ecotropic Receptor (EcoR)

Gesicles were produced from 293T cells stably expressing VSV-G as described above.

Induction of Pluripotent Stem Cells

For the generation of amphotropic induced-iPS cells, human fibroblasts were infected by the viral mix for 24 h, then replated in fibroblast medium at 3.10e4 cells per well in gelatin-coated 6-well plates, which is defined as day 0.

For the generation of ecotropic induced-iPS cells, the same protocol was followed except that gesicles containing the EcoR receptor were added to the cells 1.5 h prior to infection.

Starting from day 1 post-infection, cells were cultured for 10 days in human ES-cell media supplemented with 0.5 mM VPA, then in non-supplemented hES cell medium until emergence of iPS colonies.

To establish iPS cell lines, iPS colonies were picked about 3 to 5 weeks post-infection based on ES cell-like colony morphology. The picked colonies were subsequently expanded and maintained on mytomycin-C growth-arrested MEF feeder layers in human ES-cell media without VPA. Y-27632, a ROCK inhibitor that enhances survival of dissociated single human ES and iPS cells, was used at 10 µM to increase the seeding efficiency of iPS cells for the initial colony expansion after picking and for the first day after each passaging.

Equal numbers of clones were obtained using either the amphotropic or the ecotropic transduction protocols.

The iPS clones obtained with either protocol were expanded in hESC culture conditions for over 20 passages without any change in morphology Immunocytochemistry analysis of pluripotency markers showed equal staining for SSEA-4 in both types of clones (FIG. 18), compatible with pluripotent stem cells characteristics.

Thus, Gesicles containing the ecoptropic receptor can be used in order to render the target cells permissive to an ecotropic virus. Ecotropic viruses can then efficiently replace amphotropic vectors in order to deliver a reprogramming transcription factor to a target cell. They can be used to efficiently reprogram a somatic cell into an induced pluripotent stem cell (iPS) and represent a safer alternative.

Example 4B

Reprogramming Using Gesicles Containing C-Myc

Production of Gesicles Containing the Reprogramming Factor C-Myc

Human microvesicles were produced by transfection of HEK 293T cells using the calcium phosphate method. Cells were seeded at 3×10e6 cells in 10 cm dishes and cotransfected with 15 µg of a VSV-G encoding plasmid and 15 µg of the c-MYC encoding plasmid per dish. Transfection medium was changed 24 h latter and vesicles-containing supernatant were collected 48 hours and 72 hours after transfection, pooled, filtered through a 0.45 um filter, and ultracentrifuged 1H30 in a SW41 rotor at 25000 rpm (110000 g). Pelleted material was finally resuspended overnight in cold PBS resulting in a 200-fold concentration (supernatant vol/final vol). Preparations were performed with six 10-cm dishes and generated around 400 µl of 200× vesicles.

Cell Culture

IMR-90 human normal fibroblasts were maintained in DMEM high Glucose supplemented with 10% FBS, 1 mM sodium pyruvate and 2 mM GlutaMAX™. Human iPS cells were maintained on mytomycin-C growth-arrested MEF feeder cells in human ES cell medium, i.e. Knockout DMEM supplemented with 20% knockout serum replacement, 10 ng/ml bFGF, 0.1 mM nonessential amino acids, 50 mM β-mercaptoethanol, 2 mM GlutaMA™ and 0.1% penicillin/streptomycin.

Retrovirus Production

Moloney-based retroviral vectors (pMIGs) containing human complementary DNAs (cDNAs) of Oct-4, Sox2 and Klf4 were obtained from Addgene. These plasmids were individually transfected using FuGene into PLAT-A (for amphotropic viral production) packaging cells. PLAT-A cells medium was replaced 24 h post-transfection. Viral supernatants were collected 48 h post-transfection, filtered through a 0.45 µm filter, then mixed at a 1:1:1 ratio. Hepes and polybrene (4 µg/mL) were added to the viral mix.

Induction of Pluripotent Stem Cells

IMR-90 fibroblasts were infected by the viral mix, then 10 µL of c-Myc-containing gesicles where added to the transduction medium 6 hours after initiation of transduction. 24 h after transduction cells where replated in fibroblast medium at 3.5×10e4 cells per well in gelatin-coated 6-well plates, which is defined as day 0. At day 1 a second treatment with 10 µL of c-Myc-containing gesicles was performed.

Starting from day 1 post-infection, cells were cultured for 10 days in human ES-cell media supplemented with 0.5 mM VPA, then in non-supplemented hES cell medium until emergence of iPS colonies.

1 iPS colony was picked about 4 weeks post-infection based on ES cell-like colony morphology. The picked colony was subsequently expanded and maintained on mitomycin-C growth-arrested MEF feeder layers in human ES-cell media without VPA. Y-27632, a ROCK inhibitor that enhances survival of dissociated single human ES and iPS cells, was used at 10 µM to increase the seeding efficiency of iPS cells for the initial colony expansion after picking and for the first day after each passaging.

The iPS clone obtained with c-Myc-containing gesicles was expanded in hESC culture conditions for over 8 passages without any change in morphology. Flow cytometry analysis of pluripotency markers showed double staining for SSEA-4 and TRA-1-81 in more than 90% of the population (FIG. 19), consistent with pluripotent stem cells characteristics.

Thus, Gesicles containing a reprogramming transcription factor can efficiently replace lentiviral vectors in order to deliver a reprogramming transcription factor to a target cell. They can be used to efficiently reprogram a somatic cell into an induced pluripotent stem cell (iPS).

REFERENCES

Throughout this application, various references describe the state of the art to which this invention pertains. The disclosures of these references are hereby incorporated by reference into the present disclosure.

The invention claimed is:

1. An in vitro method for delivering a reprogramming factor into a target cell comprising i) providing an eukaryotic cell overexpressing a viral membrane fusion protein and at least one reprogramming transcription factor, wherein said eukaryotic cell secretes a microvesicle comprising said viral membrane fusion protein and said at least one reprogramming transcription factor and wherein said eukaryotic cell does not express any viral structural proteins; and ii) contacting said microvesicle to a target cell, wherein said contacting delivers said at least one reprogramming transcription factor into said target cell.

2. The method according to claim 1, wherein said viral membrane fusion protein is VSV-G.

3. The method according to claim 2, wherein said at least one transcription factor is selected from the group consisting of Oct-4, Klf4, Sox2, Lin28, and c-Myc.

4. The method according to claim 1, wherein said contacting comprises co-culturing said eukaryotic cell with said target cell.

5. A method of obtaining induced pluripotent stem cells from a target cell comprising: i) providing an eukaryotic cell overexpressing a viral membrane fusion protein and reprogramming transcription factors, where said eukaryotic cell secretes a microvesicle comprising said viral membrane fusion protein and said reprogramming transcription factors and wherein said eukaryotic cell does not express any viral structural proteins; and ii) contacting said microvesicle to a target cell, wherein said contacting delivers said reprogramming transcription factors into said target cell and reprograms said target cell into an induced pluripotent cell.

6. A method of obtaining an induced pluripotent cell comprising the steps of:
(i) contacting a target cell with a microvesicle comprising a viral fusion protein and an ecotropic viral receptor (EcoR), wherein the microvesicle delivers the EcoR into said target cell and renders said target cell permissive to an ecotropic virus; and
(ii) transducing said target cell with an ecotropic virus comprising a nucleic acid encoding reprogramming transcription factors,
wherein said target cell expresses said nucleic acid encoding reprogramming transcription factors and said reprogramming transcription factors reprogram said target cell into an induced pluripotent cell.

7. The method according to claim 6, wherein said ecotropic virus is a rodent ecotropic virus that can only replicate in a cell expressing EcoR.

* * * * *